(12) United States Patent
Kokoris et al.

(10) Patent No.: US 8,592,182 B2
(45) Date of Patent: Nov. 26, 2013

(54) HIGH THROUGHPUT NUCLEIC ACID SEQUENCING BY SPACING

(75) Inventors: Mark Stamatios Kokoris, Bothell, WA (US); Robert N. McRuer, Mercer Island, WA (US)

(73) Assignee: Stratos Genomics Inc., Seattle, WA (US)

( * ) Notice: Subject to any disclaimer, the term of this patent is extended or adjusted under 35 U.S.C. 154(b) by 407 days.

(21) Appl. No.: 12/738,884

(22) PCT Filed: Oct. 23, 2008

(86) PCT No.: PCT/US2008/081025
§ 371 (c)(1),
(2), (4) Date: Jul. 26, 2010

(87) PCT Pub. No.: WO2009/055617
PCT Pub. Date: Apr. 30, 2009

(65) Prior Publication Data
US 2010/0297644 A1  Nov. 25, 2010

Related U.S. Application Data

(60) Provisional application No. 60/981,916, filed on Oct. 23, 2007, provisional application No. 61/000,305, filed on Oct. 25, 2007.

(51) Int. Cl.
*C12P 19/34* (2006.01)
*C12Q 1/68* (2006.01)
*C07H 21/00* (2006.01)
*C07H 21/04* (2006.01)

(52) U.S. Cl.
USPC ......... 435/91.1; 435/6.1; 536/23.1; 536/24.3; 536/25.3

(58) Field of Classification Search
USPC ................ 536/23.1, 24.3, 25.3; 435/6.1, 91.1
See application file for complete search history.

(56) References Cited

U.S. PATENT DOCUMENTS

| 6,110,682 | A | 8/2000 | Dellinger et al. | |
|---|---|---|---|---|
| 8,349,565 | B2 * | 1/2013 | Kokoris et al. | 435/6.12 |
| 2004/0166505 | A1 | 8/2004 | Bruchez et al. | |
| 2005/0089890 | A1 | 4/2005 | Cubicciotti | |
| 2005/0222393 | A1 | 10/2005 | Ford et al. | |
| 2006/0228717 | A1 | 10/2006 | Joyce | |
| 2007/0190542 | A1 | 8/2007 | Ling et al. | |
| 2007/0212695 | A1 | 9/2007 | Aivazachvili et al. | |

FOREIGN PATENT DOCUMENTS

| WO | WO 95/09248 A1 | 4/1995 |
|---|---|---|
| WO | WO 2006/044994 A2 | 4/2006 |

* cited by examiner

*Primary Examiner* — Jezia Riley
(74) *Attorney, Agent, or Firm* — Seed IP Law Group PLLC

(57) ABSTRACT

Nucleic acid sequencing methods and related devices, products and kits are disclosed. Methods for sequencing a target nucleic acid comprise providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a probe and a reporter construct. The subunit encodes sequence information in its reporter construct that is less than sequence information in the corresponding portion of the target nucleic acid. The reduced information allows for reduced resolution requirements on the detection system and for increased size of resolvable reporter groups.

44 Claims, 17 Drawing Sheets

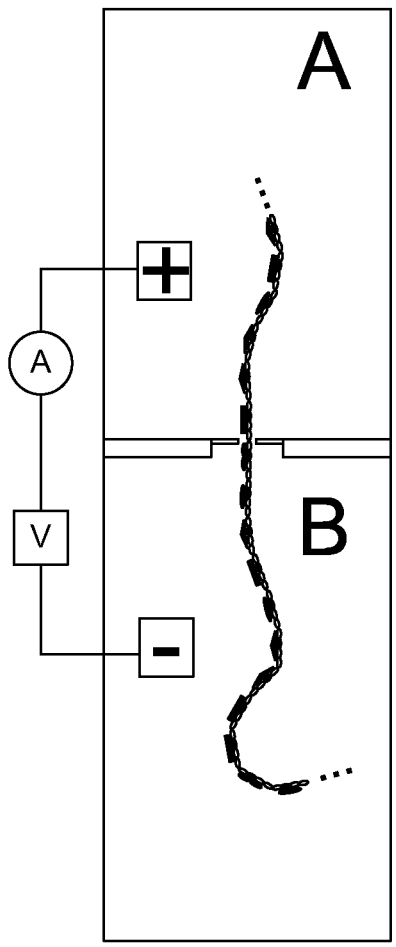 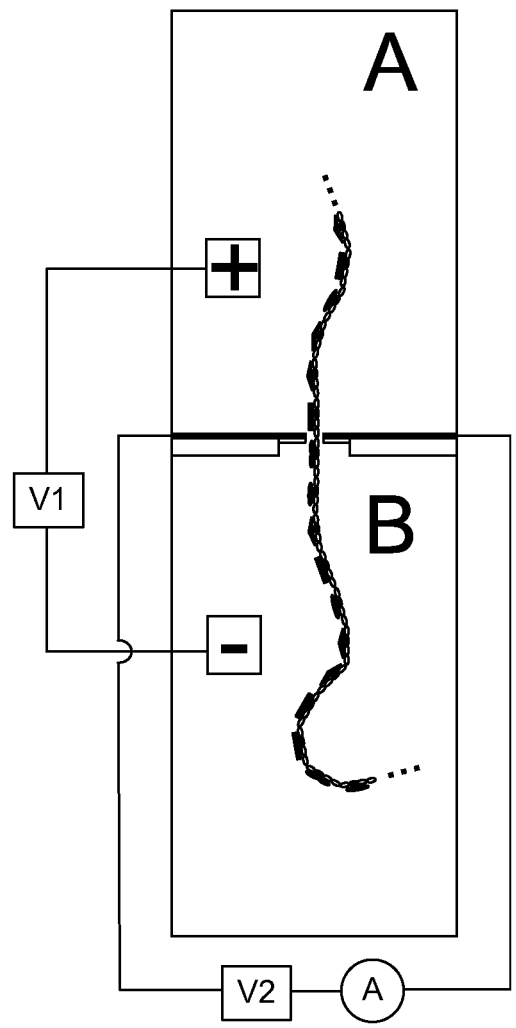
*FIG. 13*  *FIG. 14*

HIGH THROUGHPUT NUCLEIC ACID SEQUENCING BY SPACING

CROSS-REFERENCES TO RELATED APPLICATIONS

The present application claims the benefit under 35 U.S.C. §119(e) of U.S. Provisional Patent Application No. 60/981,916 filed on Oct. 23, 2007; and U.S. Provisional Patent Application No. 61/000,305 filed on Oct. 25, 2007; both of which are incorporated herein by reference in their entireties.

BACKGROUND

1. Technical Field

This invention is generally related to nucleic acid sequencing, as well as methods and products relating to the same.

2. Description of the Related Art

Nucleic acid sequences encode the necessary information for living things to function and reproduce, and are essentially a blueprint for life. Determining such sequences is therefore a tool useful in pure research into how and where organisms live, as well as in applied sciences such as drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine.

DNA sequencing is the process of determining the order of the chemical constituents of a given DNA polymer. These chemical constituents, which are called nucleotides, exist in DNA in four common forms: deoxyadenosine (A), deoxyguanosine (G), deoxycytidine (C), and deoxythymidine (T). Sequencing of a diploid human genome requires determining the sequential order of approximately 6 billion nucleotides.

Currently, most DNA sequencing is performed using the chain termination method developed by Frederick Sanger. This technique, termed Sanger Sequencing, uses sequence specific termination of DNA synthesis and fluorescently modified nucleotide reporter substrates to derive sequence information. This method sequences a target nucleic acid strand, or read length, of up to 1000 bases long by using a modified polymerase chain reaction. In this modified reaction the sequencing is randomly interrupted at select base types (A, C, G or T) and the lengths of the interrupted sequences are determined by capillary gel electrophoresis. The length then determines what base type is located at that length. Many overlapping read lengths are produced and their sequences are overlaid using data processing to determine the most reliable fit of the data. This process of producing read lengths of sequence is very laborious and expensive and is now being superseded by new methods that have higher efficiency.

The Sanger method was used to provide most of the sequence data in the Humane Genome Project which generated the first complete sequence of the human genome. This project took over 10 years and nearly $3B to complete. Given these significant throughput and cost limitations, it is clear that DNA sequencing technologies will need to improve drastically in order to achieve the stated goals put forth by the scientific community. To that end, a number of second generation technologies, which far exceed the throughput and cost per base limitations of Sanger sequencing, are gaining an increasing share of the sequencing market. Still, these "sequencing by synthesis" methods fall short of achieving the throughput, cost, and quality targets required by markets such as whole genome sequencing for personalized medicine.

For example, 454 Life Sciences is producing instruments (e.g., the Genome Sequencer) that can process 100 million bases in 7.5 hours with an average read length of 200 nucleotides. Their approach uses a variation of Polymerase Chain Reaction ("PCR") to produce a homogeneous colony of target nucleic acid, hundreds of bases in length, on the surface of a bead. This process is termed emulsion PCR. Hundreds of thousands of such beads are then arranged on a "picotiter plate". The plate is then prepared for an additional sequencing whereby each nucleic acid base type is sequentially washed over the plate. Beads with target that incorporate the base produce a pyrophosphate byproduct that can be used to catalyze a light producing reaction that is then detected with a camera.

Illumina Inc. has a similar process that uses reversibly terminating nucleotides and fluorescent labels to perform nucleic acid sequencing. The average read length for Illumina's 1G Analyzer is less than 40 nucleotides. Instead of using emulsion PCR to amplify sequence targets, Illumina has an approach for amplifying PCR colonies on an array surface. Both the 454 and Illumina approaches use a complicating polymerase amplification to increase signal strength, perform base measurements during the rate limiting sequence extension cycle, and have limited read lengths because of incorporation errors that degrade the measurement signal to noise proportionally to the read length.

Applied Biosystems uses reversible terminating ligation rather than sequencing-by-synthesis to read the DNA. Like 454's Genome Sequencer, the technology uses bead-based emulsion PCR to amplify the sample. Since the majority of the beads do not carry PCR products, the researchers next use an enrichment step to select beads coated with DNA. The biotin-coated beads are spread and immobilized on a glass slide array covered with streptavidin. The immobilized beads are then run through a process of 8-mer probe hybridization (each labeled with four different fluorescent dyes), ligation, and cleavage (between the 5th and 6th bases to create a site for the next round of ligation). Each probe interrogates two bases, at positions 4 and 5 using a 2-base encoding system, which is recorded by a camera. Similar to Illumina's approach, the average read length for Applied Biosystems' SOLiD platform is less than 40 nucleotides.

Other approaches are being developed to avoid the time and expense of the polymerase amplification step by measuring single molecules of DNA directly. Visigen Biotechnologies, Inc. is measuring fluorescently labeled bases as they are sequenced by incorporating a second fluorophore into an engineered DNA polymerase and using Forster Resonance Energy Transfer (FRET) for nucleotide identification. This technique is faced with the challenges of separating the signals of bases that are separated by less than a nanometer and by a polymerase incorporation action that will have very large statistical variation.

A process being developed by LingVitae sequences cDNA inserted into immobilized plasmid vectors. The process uses a Class IIS restriction enzyme to cleave the target nucleic acid and ligate an oligomer into the target. Typically, one or two nucleotides in the terminal 5' or 3' overhang generated by the restriction enzyme determine which of a library of oligomers in the ligation mix will be added to the sticky, cut end of the target. Each oligomer contains "signal" sequences that uniquely identify the nucleotide(s) it replaces. The process of cleavage and ligation is then repeated. The new molecule is then sequenced using tags specific for the various oligomers. The product of this process is termed a "Design Polymer" and always consists of a nucleic acid longer than the one it replaces (e.g., a dinucleotide target sequence is replaced by a "magnified" polynucleotide sequence of as many as 100 base pairs). An advantage of this process is that the duplex product strand can be amplified if desired. A disadvantage is that the process is necessarily cyclical and the continuity of the template would be lost if simultaneous multiple restriction cuts were made.

U.S. Pat. No. 7,060,440 to Kless describes a sequencing process that involves incorporating oligomers by polymerization with a polymerase. A modification of the Sanger method, with end-terminated oligomers as substrates, is used to build sequencing ladders by gel electrophoresis or capillary chromatography. While coupling of oligomers by end ligation is well known, the use of a polymerase to couple oligomers in a template-directed process was utilized to new advantage.

Polymerization techniques are expected to grow in power as modified polymerases (and ligases) become available through genetic engineering and bioprospecting, and methods for elimination of exonuclease activity by polymerase modification are already known. For example, Published U.S. Patent Application 2007/0048748 to Williams describes the use of mutant polymerases for incorporating dye-labeled and other modified nucleotides. Substrates for these polymerases also include γ-phosphate labeled nucleotides. Both increased speed of incorporation and reduction in error rate were found with chimeric and mutant polymerases.

In addition, a large effort has been made by both academic and industrial teams to sequence native DNA using non-synthetic methods. For example, Agilent Technologies, Inc. along with university collaborators are developing a single molecule detection method that threads the DNA through a nanopore to make measurements as it passes through. As with Visigen and LingVitae, this method must overcome the problem of efficiently and accurately obtaining distinct signals from individual nucleobases separated by sub-nanometer dimensions, as well as the problem of developing reproducible pore sizes of similar size. As such, direct sequencing of DNA by detection of its constituent parts has yet to be achieved in a high-throughput process due to the small size of the nucleotides in the chain (about 4 Angstroms center-to-center) and the corresponding signal to noise and signal resolution limitations therein. Direct detection is further complicated by the inherent secondary structure of DNA, which does not easily elongate into a perfectly linear polymer.

While significant advances have been made in the field of DNA sequencing, there continues to be a need in the art for new and improved methods. The present invention fulfills these needs and provides further related advantages.

BRIEF SUMMARY

In general terms, methods and corresponding devices, products and kits are disclosed that overcome the spatial resolution challenges presented by existing high throughput nucleic acid sequencing techniques. This is achieved by encoding only a subset of the nucleic acid information of a DNA target onto a surrogate polymer (daughter strand) which creates space between the detectable elements and is thus easier to "read" than its parent DNA. This sequencing technique is also referred to herein as "sequencing-by-spacing" or "SSP", and provides a daughter strand that serves as a labeled DNA surrogate ("S-polymer") which can then be measured to indirectly determine DNA sequence. The S-polymer is produced by template dependent replication of a DNA target in which a plurality of probe constructs are serially connected. Such constructs are referred to as "S-mers" or "spacer oligomers" and have at least one reporter construct that identifies nucleic acid base information. By design, only a portion of the base information is encoded to reduce the density of the reporter constructs and thereby simplify detection requirements.

In one embodiment, a method is provided for sequencing a target nucleic acid comprising providing a daughter strand (S-polymer) produced by a template-directed synthesis. This daughter strand comprises a plurality of subunits (S-mers) coupled in a sequence corresponding to a contiguous nucleotide sequence of all or a portion of the target nucleic acid. The individual subunits comprise a probe with X nucleobase residues (with X being a positive integer greater than one) and a reporter construct that encodes Y nucleobase residue(s) of the probe (with Y being a positive integer less than X). The reporter constructs are then detected to determine Y nucleobase(s) every X nucleobases of the daughter strand.

Since Y is less than X, only a fraction of the nucleotide bases are detected. For example, and for illustration only, when X is 4 and Y is 1, the reporter constructs are detected to determine 1 nucleobase every 4 nucleobases of the daughter strand. Since the daughter strand comprises a plurality of subunits coupled in a sequence corresponding to a contiguous nucleotide sequence of all or a portion of the target nucleic acid, 1 of every 4 nucleobases of the target nucleic acid is sequenced. In many instance, detection of "Y of every X" nucleobases (e.g., 1 of every 4, or every $4^{th}$, nucleobase) in the target nucleic acid is sufficient for sequencing purposes. Alternatively, and if desired, template-dependent replication of the target nucleic acid using a plurality (e.g., library) of probe constructs may be employed to produce additional daughter strands for detection, thus identifying the remaining interlaced target nucleobases in a similar manner.

The number of nucleobase residues, X, may range from 2 to 20, inclusive, and the number of encoded bases, Y, is at least 1 and generally ranges from 1 to 10. Typically, X is 2, 4, 5 or 6 and Y is 1 or 2. In the representative embodiments set forth hereinbelow for purpose of illustration (such as in the figures) X is often shown as 4 and Y as 1; however, one skilled in this field will recognize that other values for X and Y may similarly be employed. The nucleobase residues of the probe may be, for example, adenine (A), guanine (G), cytosine (C) or thymine (T), or other heterocyclice base moieties as discussed in greater detail below, including universal bases. The template-directed synthesis of the daughter strand may be accomplished by any number of methods, including techniques involving one or more enzymatic ligations, polymerase reactions and/or chemical ligations. As noted above, the daughter strand comprises a plurality of subunits, the number of which can vary widely, for example, be greater than 30, or greater than 1000.

Detection of the daughter strand can be accomplished by any of a variety of techniques. For example, the reporter constructs can be detected by passing the daughter strand through a nanopore, by interrogation with an electron beam, by scanning tunneling microscopy (STM), and/or transmission electron microscopy (TEM). The nature of the reporter construct will largely depend upon the detection method employed. The reporter construct may be joined to at least one nucleobase residue of the probe by a covalent bond. Alternatively, or in addition to, the reporter construct may be a component of at least one nucleobase residue of the probe. Further, the daughter strand can be duplexed with the target nucleic acid when the reporter constructs are detected, or the daughter strand can be disassociated from the target nucleic acid at the point of detection.

The daughter strand comprises a plurality of subunits coupled in a sequence corresponding to a contiguous nucleotide sequence of all or a portion of the target nucleic acid, and may be represented by the following structure:

wherein P represents the probe with X nucleobase residues; C represents the reporter construct that encodes Y nucleobase residue(s) of the probe; and i represents the $i^{th}$ subunit in a chain m subunits. The daughter strand may comprise any number of subunits which may be, for example, greater 10, greater than 100, or greater than 1000. Further, while the reporter construct, C, is depicted above as being joined to the probe, P, by a bond, the reporter construct can be a component of the probe itself, and depiction of the reporter construct as a separate linked moiety is for purpose of illustration only.

When the daughter strand is duplexed with the target nucleic acid, it may be represented by the following structure:

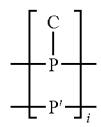

wherein P represents the probe with X nucleobase residues; P' represents a contiguous nucleotide sequence of X nucleotide residues of the template strand to which P is complementary; C represents the reporter construct that encodes Y nucleobase residue(s) of the probe; and i represents the $i^{th}$ subunit in a chain m subunits.

The daughter strand may be formed by template-directed synthesis from a plurality of constructs (S-mers) having the following structure:

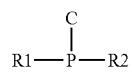

wherein R1 and R2 represent the same or different end groups for the template synthesis of the daughter strand; P represents the probe with X nucleobase residues; and C represents the reporter construct that encodes Y nucleobase residue(s) of the probe. R1 and R2 represent any number of groups suitable for this purpose, as set forth in greater detail below. In an alternative embodiment, the reporter construct is added to the daughter strand after template-directed synthesis thereof, and the plurality of constructs have the same structure as above, but lacking the reporting construct.

In another embodiment, a kit is disclosed comprising a plurality of constructs (i.e., S-mers with the appropriate R1/R2 end groups) for forming a daughter strand by a template-directed synthesis, and may optionally comprise appropriate instructions for use of the same in forming a daughter strand. The number of constructs of the kit (which may also be referred to as a "library" of constructs) will depend upon the value of X, as well as the number of universal bases employed as the nucleobases residue(s). For example, such a kit or library of constructs may contain unique members numbering, for example, from 10 to 65000, from 50 to 5000, or from 200 to 1200.

These and other aspects of the invention will be apparent upon reference to the attached drawings and following detailed description. To this end, various references are set forth herein which describe in more detail certain procedures, compounds and/or compositions, and are hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 5A illustrates a partial duplex template with a twenty base 5' overhang to demonstrate processive ligation of substrates, while

FIG. 13 illustrates a conventional nanopore detection method.

FIG. 14 illustrates a transverse electrode nanopore detection method.

DETAILED DESCRIPTION

Figure 1A:
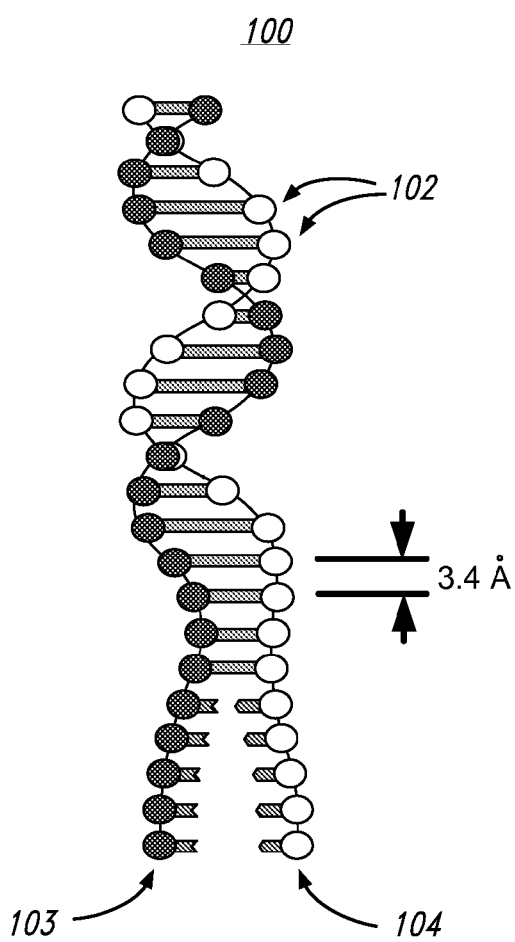
FIG. 1A illustrates the limited separation between nucleobases that must be resolved in order to determine the sequence of nucleotides in a nucleic acid target.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, and unless the context dictates otherwise, the following terms have the meanings as specified below.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N-6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, La.), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Polynucleotides", also called nucleic acids, are covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. Oligonucleotides are generally shorter chained polynucleotides.

"Complementary" generally refers to specific nucleotide duplexing to form canonical Watson-Crick base pairs, as is understood by those skilled in the art. However, complementary as referred to herein also includes base-pairing of nucleotide analogs, which include, but are not limited to, 2'-deoxyinosine and 5-nitroindole-2'-deoxyriboside, which are capable of universal base-pairing with A, T, G or C nucleotides and locked nucleic acids, which enhance the thermal stability of duplexes. One skilled in the art will recognize that hybridization stringency is a determinant in the degree of match or mismatch in the duplex formed by hybridization.

"Nucleic acid" is a polynucleotide or an oligonucleotide. A nucleic acid molecule can be deoxyribonucleic acid (DNA), ribonucleic acid (RNA), or a combination of both. Nucleic acids are generally referred to as "target nucleic acids" or "target sequence" if targeted for sequencing. Nucleic acids can be mixtures or pools of molecules targeted for sequencing.

"Probe" is a short strand of nucleobase residues, referring generally to two or more contiguous nucleobase residues, which are generally single-stranded and complementary to a target sequence of a nucleic acid. As embodied in "S-mers", probes can range from 2 to more than 20, and typically are 2 to 20 nucleobase residues in length. Probes may include modified nucleobase residues and modified intra-nucleobase bonds in any combination. Backbones of probes can be linked together by any of a number of types of covalent bonds, including, but not limited to, ester, phosphodiester, phosphoramide, phosphonate, phosphorothioate, phosphorothiolate, amide bond and any combination thereof. The probe may also have 5' and 3' end linkages that include, but are not limited to, the following moieties: monophosphate, triphosphate, hydroxyl, hydrogen, ester, ether, glycol, amine, amide, and thioester.

"Selective hybridization" refers to specific complementary binding. Polynucleotides, oligonucleotides and probes, that may contain one or more universal bases, selectively hybridize to target nucleic acid strands, under hybridization and wash conditions that minimize nonspecific binding. As known in the art, high stringency conditions can be used to achieve selective hybridization conditions favoring a perfect match. Conditions for hybridization such as salt concentration, temperature, detergents, PEG, and GC neutralizing agents such as betaine can be varied to increase the stringency of hybridization, that is, the requirement for exact matches of C to base pair with G, and A to base pair with T or U, along a contiguous strand of a duplex nucleic acid.

"Template-directed synthesis", "template-directed assembly", "template-directed hybridization", "template-directed binding" and any other template-directed processes, refer to a process whereby probes bind selectively to a complementary target nucleic acid, and are incorporated into a nascent daughter strand. "Template-directed polymerization" and "template-directed ligation" are special cases of template-directed synthesis whereby the resulting daughter strand is polymerized or ligated, respectively.

A "daughter strand" is produced by a template-directed process and is generally complementary to the target single-stranded nucleic acid from which it is synthesized. An S-polymer is a daughter strand of its target nucleic acid.

"Contiguous" indicates that a sequence continues without interruption or missed nucleobase. The contiguous sequence of nucleotides of the template strand is said to be complementary to the contiguous sequence of the daughter strand.

"Substrates" are probes that have binding specificity to the target template. The substrates are generally combined with reporter constructs form S-mers. S-mers substrates that form the daughter strand (called the S-polymer) are also substrates of the daughter strand.

"S-mers" are reagents for template-directed synthesis of daughter strands (S-polymers), and are generally provided in the form of libraries. S-mers contain a probe substrate for complementary binding to a target template and one or more reporter constructs. The reporter construct encodes some of the substrate base information. S-mers are provided in a variety of forms adapted to the invention. In one embodiment, S-mers have reporter constructs that link to reporters after the S-polymer is synthesized. S-mer probes with 5'-monophosphate and 3'OH modifications are compatible with enzymatic ligation-based methods for S-polymer synthesis. S-mer probes with 5' and 3' linker modifications are compatible with chemical ligation-based methods for S-polymer synthesis. S-mer probes with 5'-triphosphate and 3'-OH are compatable with enzymatic polymerization.

"Subunit motif" or "motif" refers to a repeating subunit of a polymer backbone, the subunit having an overall form characteristic of the repeating subunits, but also having species-specific elements that encode genetic information. Motifs of complementary nucleobase residues are represented in libraries of S-mers according to the number of possible combinations of the basic complementary sequence binding nucleobase elements in each motif. If the nucleobase binding elements are four (e.g., A, C, G, and T), the number of possible motifs of combinations of four elements is $4^x$, where x is the number of nucleobase residues in the motif. However, other motifs based on degenerate pairing bases, on universal bases, on the substitution of uracil for thymidine in ribonucleobase residues or other sets of nucleobase residues, can lead to larger or smaller libraries of motif-bearing S-mers. Multiple motifs may have the same reporter construct. Generally, an S-mer is associated with a single reporter construct and generally that reporter construct encodes for 1 base in the S-mer probe. Multiple motifs may have the same encoded base.

"Primary backbone" refers to a contiguous or segmented backbone of substrates of the daughter strand (S-polymer). A commonly encountered primary backbone is the ribosyl 5'-3' phosphodiester backbone of a native polynucleotide. However, the primary backbone of an daughter strand may contain analogs of nucleobases and analogs of oligomers not linked by phosphodiester bonds or linked by a mixture of phosphodiester bonds and other backbone bonds, which include, but are not limited to following linkages: phosphorothioate, phosphorothiolate, phosphonate, phosphoramidate, and peptide nucleic acid "PNA" backbone bonds which include phosphono-PNA, serine-PNA, hydroxyproline-PNA, and combinations thereof. Where the daughter strand is in its duplex form (i.e., duplex daughter strand), and substrates are not covalently bonded between the subunits, the substrates are nevertheless contiguous and form the primary backbone of the daughter strand.

"S-polymer" or "S-polymer product" is a synthetic molecular construct synthesized by template-directed assembly of S-mers. The S-polymer is designed to have a sequence of reporters along its length that identifies a subset of the bases at regular spaced intervals along the target template. The linear density of the sequence information in the S-polymer reporters is lower than that of the target template because it provides only a subset. This means that reporters can be larger and more spatially separated which improves the signal to noise when the reporters are measured. The S-polymer has a backbone of linked nucleobase residues.

"Moiety" is one of two or more parts into which something may be divided, such as, for example, the various parts of a probe.

"Tether" refers to a polymer or molecular construct having a generally linear dimension and with an end moiety at each of two opposing ends. A tether optionally comprises a reporter construct for attaching to the probe in an S-mer. More than one tether may secure a reporter construct to the probe.

"Peptide nucleic acid" or "PNA" is a nucleic acid analog having nucleobase residues suitable for hybridization to a nucleic acid, but with a backbone that comprises amino acids or derivatives or analogs thereof.

"Phosphono-peptide nucleic acid" or "pPNA" is a peptide nucleic acid in which the backbone comprises amino acid analogs, such as N-(2-hydroxyethyl)phosphonoglycine or N-(2-aminoethyl)phosphonoglycine, and the linkages between nucleobase units are through phosphonoester or phosphonoamide bonds.

"Serine nucleic acid" or "SerNA" is a peptide nucleic acid in which the backbone comprises serine residues. Such residues can be linked through amide or ester linkages.

"Hydroxyproline nucleic acid" or "HypNA" is a peptide nucleic acid in which the backbone comprises 4-hydroxyproline residues. Such residues can be linked through amide or ester linkages.

"Reporter element" is a signaling element, molecular complex, compound, molecule or atom that is also comprised of an associated "reporter detection characteristic". Other reporter elements include, but are not limited to, FRET resonant donor or acceptor, dye, quantum dot, bead, dendrimer, up-converting fluorophore, magnet particle, electron scatterer (e.g., boron), mass, gold bead, magnetic resonance, ionizable group, polar group, hydrophobic group. Still others are fluorescent labels, such as but not limited to, ethidium bromide, SYBR Green, Texas Red, acridine orange, pyrene, 4-nitro-1,8-naphthalimide, TOTO-1, YOYO-1, cyanine 3 (Cy3), cyanine 5 (Cy5), phycoerythrin, phycocyanin, allophycocyanin, FITC, rhodamine, 5(6)-carboxyfluorescein, fluorescent proteins, DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein or lanthamides; also radioisotopes (such as $^{33}P$, $^{3}H$, $^{14}C$, $^{35}S$, $^{125}I$, $^{32}P$ or $^{131}I$), ethidium, Europium, Ruthenium, and Samarium or other radioisotopes; or mass tags, such as, for example, pyrimidines modified at the C5 position or purines modified at the N7 position, wherein mass modifying groups can be, for examples, halogen, ether or polyether, alkyl, ester or polyester, or of the general type XR, wherein X is a linking group and R is a mass-modifying group, chemiluminescent labels, spin labels, enzymes (such as peroxidases, alkaline phosphatases, beta-galactosidases, and oxidases), antibody fragments, and affinity ligands (such as an oligomer, hapten, and aptamer).

A "reporter" is composed of one or more reporter elements. Reporters include what are known as "tags" and "labels." The probe of the S-mer can be considered a reporter. Reporters serve to encode the genetic information of the target nucleic acid.

"Reporter construct" comprises one or more reporters that can produce a detectable signal(s), wherein the detectable signal(s) generally contains sequence information. This signal information is termed the "reporter code" and is subsequently decoded into genetic sequence data. A reporter construct may also comprise tethers or other architectural components including polymers, graft copolymers, block copolymers, affinity ligands, oligomers, haptens, aptamers, dendrimers, linkage groups or affinity binding group (e.g., biotin). These include, but are not limited to: polyethylene glycols, polyglycols, polypyridines, polyisocyanides, polyisocyanates, poly(triarylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments. In some cases a variation on a reporter construct has unique linkages that serve to connect to reporters after the S-polymer is created.

"Reporter detection characteristic" referred to as the "signal" describes all possible measurable or detectable elements, properties or characteristics used to communicate the genetic sequence information of a reporter directly or indirectly to a measurement device. These include, but are not limited to, fluorescence, multi-wavelength fluorescence, emission spectrum fluorescence quenching, FRET, emission, absorbance, reflectance, dye emission, quantum dot emission, bead image, molecular complex image, magnetic susceptibility, electron scattering, ion mass, magnetic resonance, molecular complex dimension, molecular complex impedance, molecular charge, induced dipole, impedance, molecular mass, quantum state, charge capacity, magnetic spin state, inducible polarity, nuclear decay, resonance, or complementarity.

"Reporter Code" is the genetic information from a measured signal of a reporter construct. The reporter code is decoded to provide sequence-specific genetic information data.

"Processive" refers to a process of coupling of substrates, which is generally continuous and proceeds with directionality. While not bound by theory, both ligases and polymerases, for example, exhibit processive behavior if substrates are added to a nascent daughter strand incrementally without interruption. The steps of hybridization and ligation, or hybridization and polymerization, are not seen as independent steps if the net effect is processive growth of the nascent daughter strand. Some but not all primer-dependent processes are processive.

"Promiscuous" refers to a process of coupling of substrates that proceeds from multiple points on a template at once, and is not primer dependent, and indicates that chain extension occurs in parallel (simultaneously) from more than one point of origin.

"Single-probe extension" refers to a cyclical stepwise process in which probe substrates are added one by one. Generally the coupling reaction is restrained from proceeding beyond single substrate extension in any one step by use of reversible blocking groups.

"Corresponds to" or "corresponding" is used here in reference to a contiguous single-stranded sequence of a probe, oligonucleotide, oligonucleotide analog, or daughter strand that is complementary to, and thus "corresponds to", all or a portion of a target nucleic acid sequence. The complementary sequence of a probe can be said to correspond to its target. In general, both the complementary sequence of the probe and the complementary sequence of the target are individually contiguous sequences.

"Ligase" is an enzyme generally for joining 3'-OH 5'-monophosphate nucleotides, probes, oligomers, and their analogs. Ligases include, but are not limited to, $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

"Polymerase" is an enzyme generally for joining 3'-OH 5'-triphosphate nucleotides, probes, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tfl DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

"Encode" or "parse" are verbs referring to transferring from one format to another, and refer to transferring the genetic information of target template base sequence into an arrangement of reporters.

"Solid support" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, polystyrene, polypropylene, polycarbonate, or polyallomer. A solid support can also be a bead, resin or particle of any shape. Such particles or beads can be comprised of any suitable material, such as glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

"Reversibly blocking" or "terminator" refers to a chemical group that when bound to a second chemical group on a moiety prevents the second chemical group from entering into particular chemical reactions. A wide range of protecting groups are known in synthetic organic and bioorganic chemistry that are suitable for particular chemical groups and are compatible with particular chemical processes, meaning that they will protect particular groups during those processes and may be subsequently removed or modified (see, e.g., Metzker et al. Nucleic Acids Res., 22(20): 4259, 1994).

"Linker" is a molecule or moiety that joins two molecules or moieties, and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleobases and S-mers of interest can be accomplished through the use of coupling reagents that are known in the art (see, e.g., Efimov et al., Nucleic Acids Res. 27: 4416-4426, 1999). Methods of derivatizing and coupling organic molecules are well known in the arts of organic and bioorganic chemistry. A linker may also be cleavable or reversible.

As mentioned above, methods and corresponding devices, products and kits are disclosed that overcome the spatial resolution challenges presented by existing high throughput nucleic acid sequencing techniques, resulting in increased throughput and accuracy. This is achieved by encoding only a subset of the nucleic acid information of a DNA target onto a surrogate polymer (daughter strand) which creates space between the detectable elements and is thus easier to "read" than its parent DNA. This sequencing technique is also referred to herein as "sequencing-by-spacing" or "SSP", and provides a daughter strand that serves as a labeled DNA surrogate ("S-polymer") which can then be measured to indirectly determine DNA sequence. The S-polymer is produced by template dependent replication of a DNA target in which a plurality of probe constructs are serially connected. Such constructs are referred to as space oligomers ("S-mers") and have at least one reporter construct that identifies nucleic acid base information. By design, only a portion of the base information is encoded to reduce the density of the reporter constructs and thereby simplify detection requirements.

As shown in FIG. 1A, native duplex nucleic acids have an extremely compact linear data density; about a 3.4 Å center-to-center separation between sequential stacked bases (102) of each strand of the double helix (100), and are therefore tremendously difficult to directly image or sequence with any accuracy and speed. When the double-stranded form is denatured to form single stranded polynucleotides (103,104), the resulting base-to-base separation distances are similar, but the problem becomes compounded by domains of secondary structure.

Figure 1B:
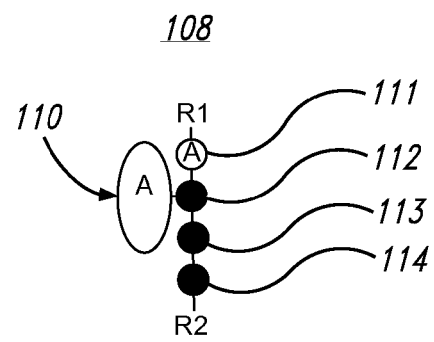
FIG. 1B is a representative S-mer.
Figure 1C:
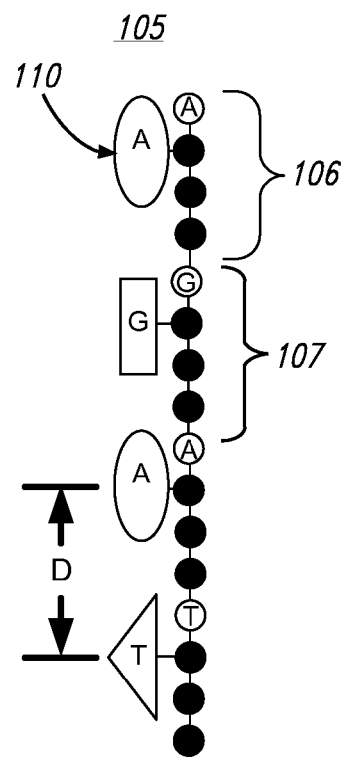
FIG. 1C illustrates schematically how S-mers can reduce resolution requirements.

FIG. 1C shows a daughter strand or S-polymer (105), here illustrated as a concatenation of short probe constructs called S-mers (106,107). FIG. 1B illustrates an S-mer (108) prior to formation of the S-polymer (i.e., the construct prior to formation of the daughter strand). It is shown here constructed of a 4-base probe (111,112,113,114) coupled to reporter construct (110). Two probe end groups R1 and R2 are used in the assembly step of the S-polymer. The S-polymer is a synthetic daughter strand complementary to the nucleic acid target to be sequenced. Bases complementary to the template nucleic acid are incorporated into the S-polymer, but in this example, only one base from each probe is identified by the associated reporter constructs. The reporter constructs (here depicted as ellipses, triangles and rectangles) can use the lineal space provided by the length of the probe (here each shown with four nucleobases depicted by circles) to avoid overlapping with reporter constructs of adjacent probes. The S-polymer is a daughter strand made by template-dependent replication of the template nucleic acid strand. This daughter strand has a contiguous linear backbone formed by these probes and thus forms a serial sequence of reporter constructs that encodes the base sequence of every $4^{th}$ base in the template nucleic acid. If desired, the full template sequence may be determined by synthesizing additional S-polymers where the starting point of the S-polymer assembly on the template is shifted appropriately (a shift of 1, 2 and 3 bases, for example). This process will be explained in more detail below, but it should be noted that the choice of four nucleobases per probe and details of the reporter construct as shown in FIGS. 1B and 1C are for purpose of illustration only, and in no way should be construed to limit the invention.

The separation distance "D" between neighboring probes in the S-polymer depends upon the number of bases in the probe and the degree of stretch in the polymer. As shown in FIGS. 1C, D for the 4-base probe is ~15 Angstroms. S-mers comprise a probe and a reporter construct that encodes a portion of the probe's nucleic acid information into some measurable characteristic. S-mers are the building blocks from which the S-polymer is made. S-mer probes as long as 4, 10 or 20 bases long will increase the space available for the reporter construct(s) to ~15, 35, and 70 Angstroms, respectively. As the separation distance increases, the process of measuring or "resolving" the sequential reporter constructs becomes easier because reporter constructs can be larger, and thus detection resolution requirements reduced.

Referring again to FIG. 1A, native DNA replicates by a process of semi-conservative replication; each new DNA molecule is a "duplex" of a template strand (103) and a native daughter strand (104). The sequence information is passed from the template to the native daughter strand by a process of "template-directed synthesis" that preserves the genetic information inherent in the sequence of the base pairs. The native daughter strand in turn becomes a template for a next generation native daughter strand, and so forth. S-polymers are formed by a similar process of template-directed synthesis, which can be an enzymatic or a chemical coupling process. However, unlike native DNA, S-polymers only require bases with the base information carried in the reporter constructs to be replicated with high fidelity. The remaining bases may be degenerate, modified, universal or subject to some mismatch provided they continue to maintain proper spacing of the bases and do not deleteriously inhibit the template-directed replication process.

FIGS. 2A through 2E show representative S-mers (201, 202, 203, 204, 205). These are the building blocks from which S-polymer (daughter strands) are synthesized. S-mers shown here have two functional components; namely, a probe portion (210) and a "reporter construct" member (220). These S-mers can be end modified with R-groups (shown as R1 and R2); for example, as a 5'-monophosphate, 3'-OH suitable for use with a ligase or as a 5'-triphosphate, 3'-OH suitable for use with a polymerase. Other R groups may be of use in various protocols.

As discussed below, a ligase-dependent process may be used to synthesize an S-polymer from a template strand of a target nucleic acid. For example, four nucleobase residues of the probe are generally complementary to a contiguous sequence of four nucleotides of the template nucleic acid. Each probe is thus designed to hybridize with the template when its sequence is complementary. By supplying a library of many such probe sequences, a contiguous complementary replica of the template can be formed. This daughter strand is termed an "S-polymer". S-polymers can have duplex or single-stranded forms.

Figure 2A:
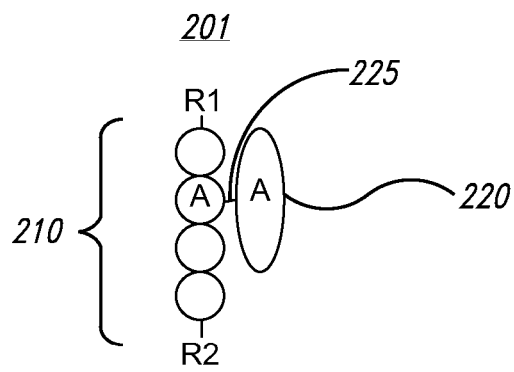
FIGS. 2A through 2E illustrate schematically several representative S-mer structures useful in the invention.
Figure 2B:
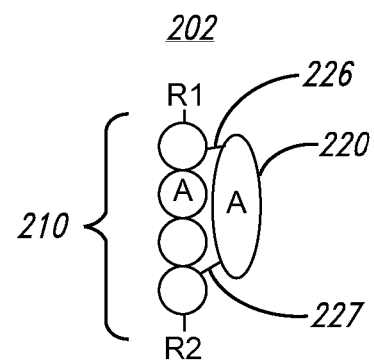

The S-mer (201) shown in FIG. 2A has a reporter construct (220) (shown as an ellipses) with a single tether attachment (225). For the S-mer (202) of FIG. 2B, the reporter construct (220) has 2 tether attachments (226, 227) to the probe. The combination of reporter elements that collectively form a "reporter construct" will produce a unique digital reporter code when detected that has sequence information. The reporter construct may use, for example, dendrimer(s), polymer(s), branched polymer(s) or combinations therein as scaffolding to attach reporters. These reporter elements include, but are not limited to, fluorophores, FRET tags, beads, ligands, aptamers, peptides, haptens, oligomers, polynucleotides, dendrimers, stem-loop structures, affinity labels, mass tags, and the like.

Figure 2C:
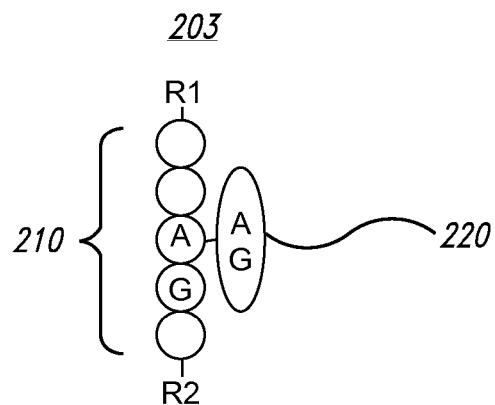
Figure 2D:
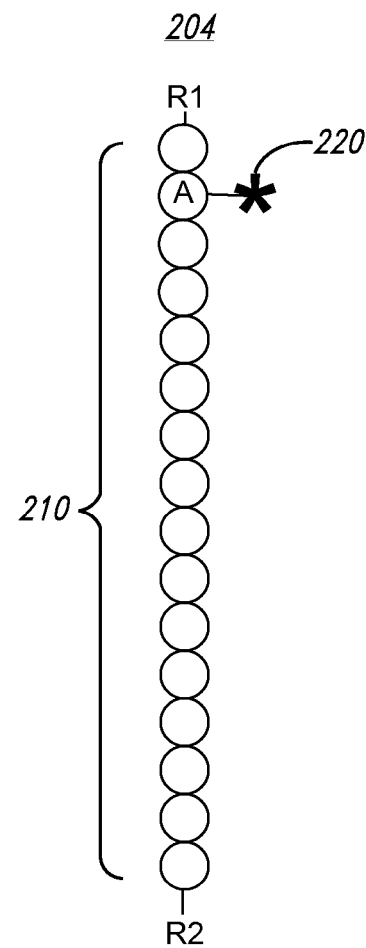
Figure 2E:
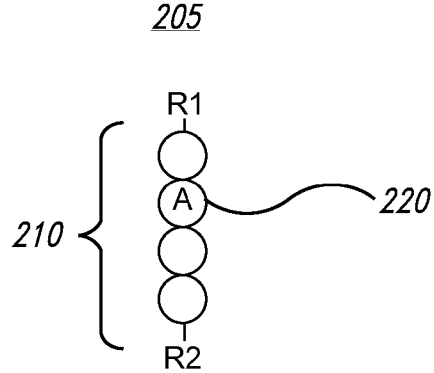

The S-mer of FIG. 2C shows that the sequence information of two bases (A and G) encoded in the reporter construct (220). This choice of encoding 2 bases per S-mer has benefits in reconstructing the sequence after detection because of how its information will overlap with other sequence data. S-mer (204) of FIG. 2D illustrates two concepts: namely, that the S-mers can be much longer to provide more linear space for resolving sequential reporter constructs, and that the sequence information (as indicated by the asterisk (*)) of the probe may be encoded in the S-mer in a modified form more readily detected in a sequencing protocol. Because the sequence data is physically more resolvable, the asterisk (*) represents any form of encoded genetic information for which this is a benefit. The elements (*) of the S-mer, whatever their form, can be reporters that are directly detectable or can be precursors to which reporters are added in a post-assembly labeling step. In some instances, the genetic information is encoded in a molecular property of the S-mer itself, for example a multi-state mass tag. In other instances, the genetic information is encoded by one or more fluorophores of FRET donor/acceptor pairs, or a nanomolecular barcode, or a ligand or combination of ligands, or in the form of some other labeling technique drawn from the art. As depicted in FIG. 2E, in some embodiments, the reporter construct is the probe itself. In this example, one base of a 4-base probe is encoded in the structure of the probe. For each of the 4 encoded bases a class of degenerate probes exists that shares a unique signature that identifies its encoded base. Various embodiments of reporter constructs will be discussed in more detail below.

It can be seen that if each substrate of a S-mer contains X nucleobases, then a library representing all possible sequential combinations of X nucleobases would contain $4^X$ probes (when selecting the nucleobases from A, T, C or G). Fewer or more combinations can be needed if other bases, including universal bases, are used. These probe substrate libraries are designed so that each S-mer contains: (1) a probe complementary to any one of the possible target sequences of the nucleic acid to be sequenced, and (2) a unique reporter construct that encodes the identity of a selected portion of target sequence which that particular probe (or nucleobase) is complementary to. For example a library of probes containing three nucleobases that used only A, C, T and G would have 64 unique members. If the S-mers using these probes encoded for the base at the 5' end of the probe, then 16 of the 64 probes would be encoded for each of the base type.

Figure 3A:
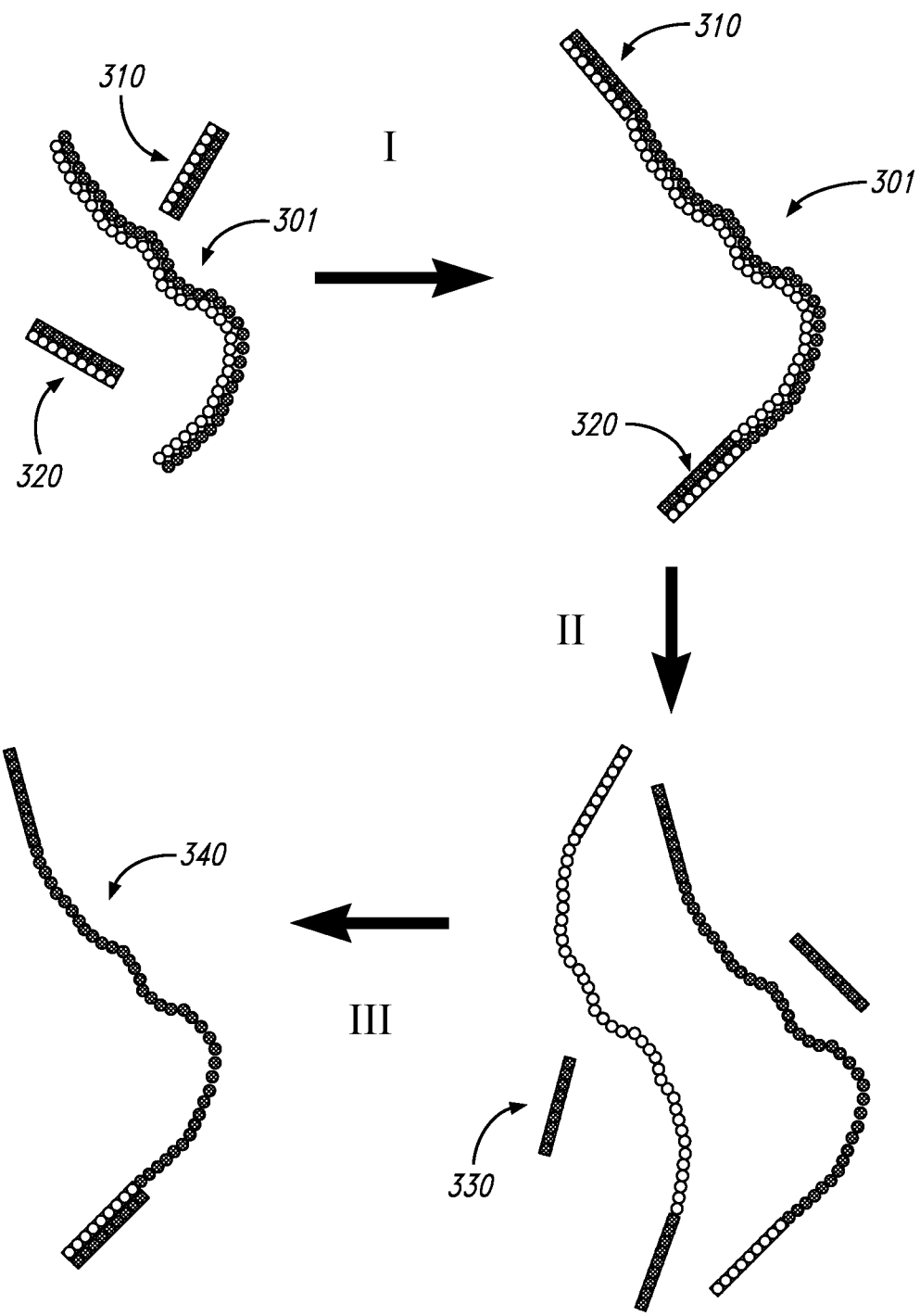
FIGS. 3A and 3B are schematics illustrating simplified steps for synthesizing an S-polymer from a target nucleic acid using progressive ligation.
Figure 3B:
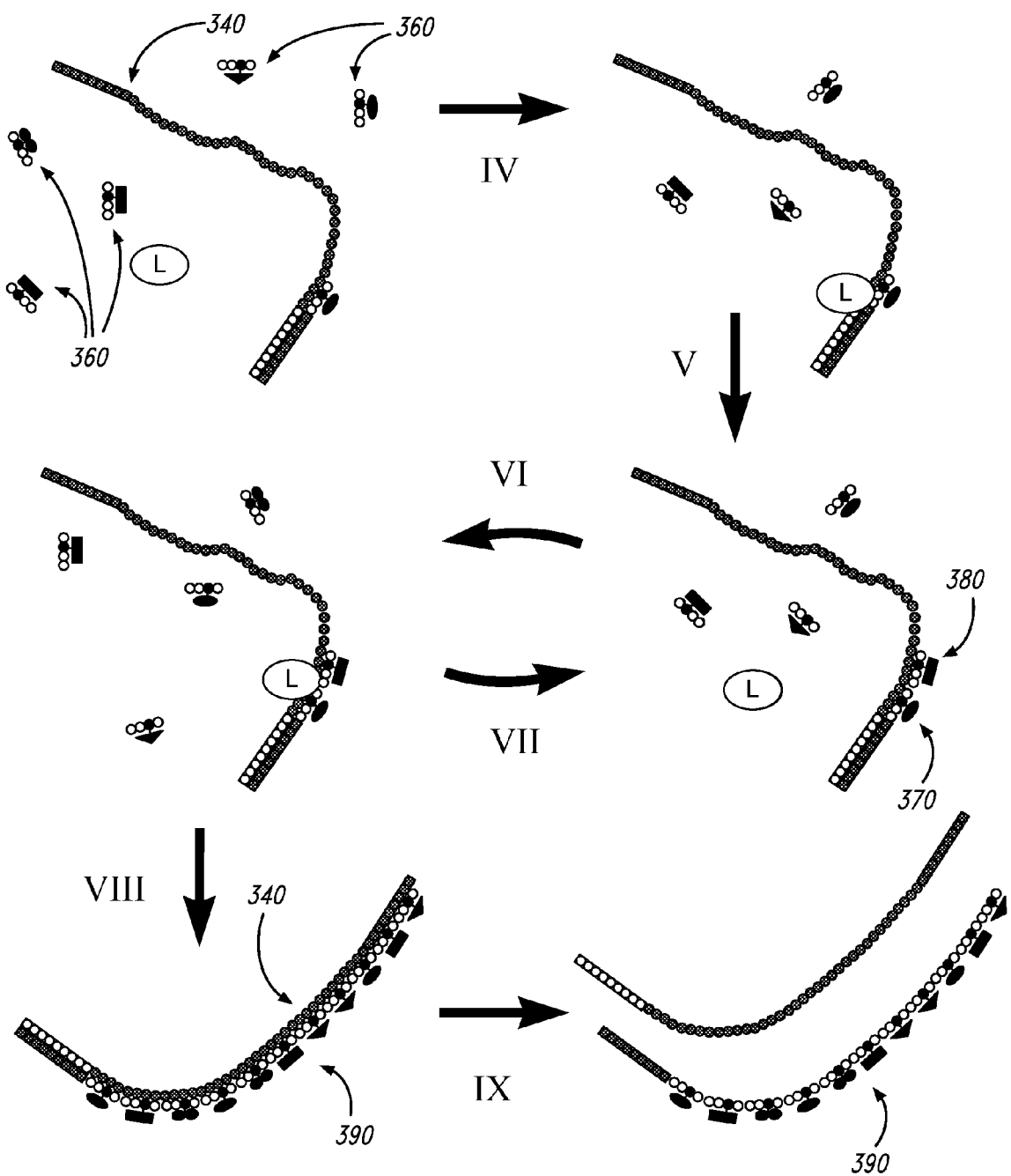

Synthesis of a representative S-polymer is illustrated in FIGS. 3A and 3B. In this case, the synthesis method is described as hybridization with primer-dependent processive ligation in free solution.

As shown in FIG. 3A, the target DNA is first prepared. Many well known molecular biological protocols, such as protocols for fragmenting the target DNA and ligating end adaptors, can be adapted for use in sequencing methods and are used here to prepare the target DNA (301) for sequencing. Here we illustrate, in broad terms that would be familiar to those skilled in the art, namely, processes for polishing the ends of the fragments and blunt-ended ligation of adaptors (310, 320) designed for use with sequencing primers. These actions are shown in Step I of FIG. 3A. In Steps II and III, the target nucleic acid (301) is denatured and annealed with suitable primers (330) complementary to the adaptors. Several alternative priming methods can be adapted for use that include duplex hairpin primers, probe-based priming, degenerate universal primers or random priming. Many of these priming methods are well known and practiced.

In FIG. 3B, the primed template strand (340) (from FIG. 3A, Step III) is contacted with a library of S-mers (360) and ligase (L). In Step IV conditions are adjusted to favor hybridization followed by ligation at a free 3'-OH of a primer-template duplex. Generally, hybridization and ligation is performed at a temperature greater than the melting temperature of the probe substrate to reduce non-specific side reactions. Optionally in Step V the ligase dissociates, and in Steps VI and VII, a cyclical process of hybridization and ligation can be recognized to result in extension by cumulative addition of S-mers (370, 380) to the primer end. Although priming can occur from adaptors at both ends of a single stranded template, the growth of a nascent S-polymer daughter strand is shown here to proceed from a single primer, solely for simplicity. Extension of the daughter strand is represented in Steps VI and VII, which are continuously repeated (incrementally, without interruption). These reactions occur in free solution and proceed until a sufficient amount of product has been synthesized. In Step VIII, formation of a completed S-polymer (390) is shown duplexed to the template strand (340). Step IX of FIG. 3B shows denaturation of the duplex to yield S-polymer (390) in a non-duplexed form. This step is optional and depends upon whether the duplex or single strand S-polymer gives better results through to the end of the detection step.

The choices of Ligases for this process include, but are not limited to, NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

Relatively long lengths of nucleotide sequence can be efficiently replicated in this manner to form the S-polymers. It can be seen that continuous read lengths that represent regular sampling of base information along long template strand fragments can be achieved with this technology. It will be apparent to one skilled in the art that billions of these single molecule SSP reactions can be done simultaneously in an efficient batch process in a single tube. Subsequently, the shotgun products of these syntheses can be sequenced.

Refinements of the basic process, such as wash steps and adjustment of conditions of stringency are well within the skill of an experienced molecular biologist. Variants on this process include, for example, immobilization and parsing of the target strands, stretching and other techniques to reduce secondary structure during synthesis of the S-polymer, post-synthesis labeling, end-functionalization, and alternatives to ligase for linking the substrates will be discussed in the materials that follow.

Synthesis of S-polymers is done to facilitate the detection and sequencing of nucleic acids, and is applicable to nucleic acids of all kinds. The process encodes sequence information at a lower linear density (relative to the small nucleotide-to-nucleotide distances of native nucleic acids) and optionally also increases signal-to-noise in detection (relative to the nearly indistinguishable, low-intensity signals observed for native nucleotides). As such, signals from the reporter constructs incorporated along the S-polymer backbone can be detected and decoded using a variety of detection methods, including detection methods well known in the art (for example, FRET-based microscopy, atomic force microscopy, or electron microscopy) as well as by methods such as parallel nanopore sensor array, or combinations of methods. Detection techniques are selected on the basis of optimal signal to noise, throughput, cost, and like factors.

Figure 3C:
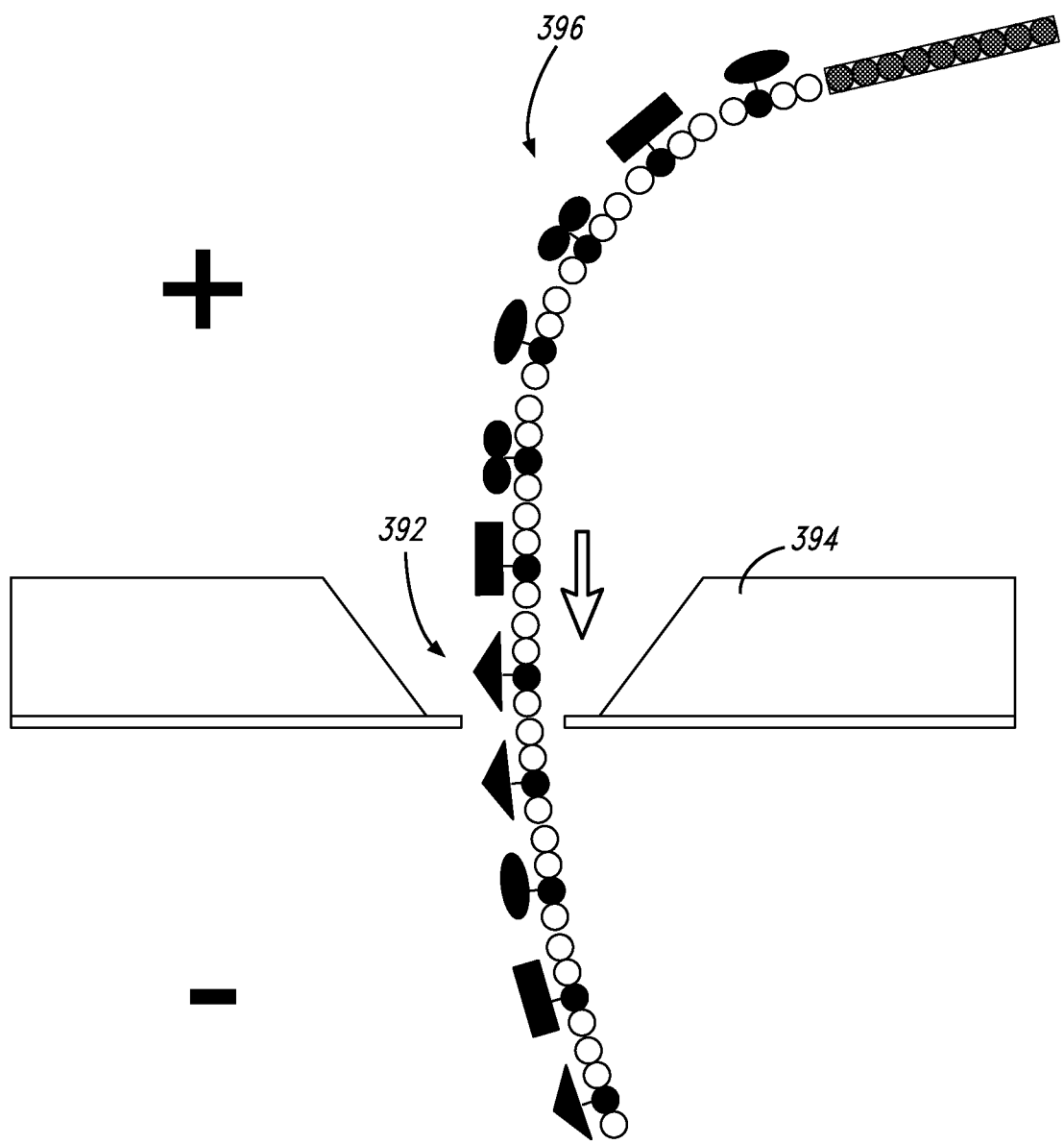
FIG. 3C is a simple model illustrating a nanopore-type device for reading S-polymers.

FIG. 3C depicts a schematic for using nanopore detection technology with S-polymers. A nanopore (392) in a thin film (394) is shown separating two reservoirs that are filled with an aqueous electrolyte solution (typically 1 molar KCl). A potential is applied between electrodes placed in each reservoir and a current flows through the nanopore. The S-polymer product (396) (shown in the non-duplexed form) has a negative charge density along its length. It is drawn into the nanopore and is pulled through by electrophoretic and/or electroosmotic forces. The nanopore current is modulated by whatever portion of the S-polymer lies within the nanopore channel. In this illustration, each reporter construct is encoded for a particular base type by using molecular structures with different molecular size and charge distribution. As each reporter construct passes through the nanopore its molecular characteristics alter the current in time and amplitude so the encoded base identity can be determined by the current measurement. By capturing this analog current signal and digitally processing it, the sequence information encoded in the sequential reporter constructs is determined. It should be noted that in this detection method, the many nanopore channels could be measured in parallel to increase throughput. Developments in nanopore technology have demonstrated measurement of single stranded RNA using biological pores of hemolysin, which could not distinguish individual bases, but could discriminate 50 base homopolymers (Butler, T. Z. et al., "Determination of RNA Orientation during Translocation through a Biological Nanopore," *Biophys. J.* 90(1): 190-199, 2006). Both single and double stranded DNA have been detected using solid state pores (Fologea, D et al., "Detecting Single Stranded DNA with a Solid State Nanopore," *Nano Letters* 5(10): 1905-1909, 2005; Storm, A. J. et al., "Translocation of double-strand DNA through a silicon oxide nanopore," *Physical Review. E, Statistical, Nonlinear, and Soft Matter Physics* 71(5 Pt 1): 051903, 2005), but have not discriminated individual bases sequentially. Other relevant nanopore sequencing technology is disclosed (Fologea, D. et al., "Electrical characterization of protein molecules by a solid-state nanopore," *Applied Physics Letters* 91(5): 053901-3, 2007; Fologea, D. et al., "DNA conformation and base number simultaneously determined in a nanopore," *Electrophoresis* 28(18): 3186-3192, 2007; Tabard-Cossa, V. et al., "Noise Analysis and reduction in solid-state nanopores," *Nanotechnology* 18(30): 305505, 2007; Smeets, R. et al., "Salt Dependence of Ion Transport and DNA Translocation through Solid-State Nanopores," *Nano Letters* 6(1): 89-95, 2006; Soni, G. V. et al., "Progress toward Ultrafast DNA Sequencing Using Solid-State Nanopores," *Clin Chem* 53(11): 1996-2001, 2007; Bezrukov, S. M. et al., "Counting polymers moving through a single ion channel," *Nature* 370 (6487): 279-281, 1994).

Figure 4:
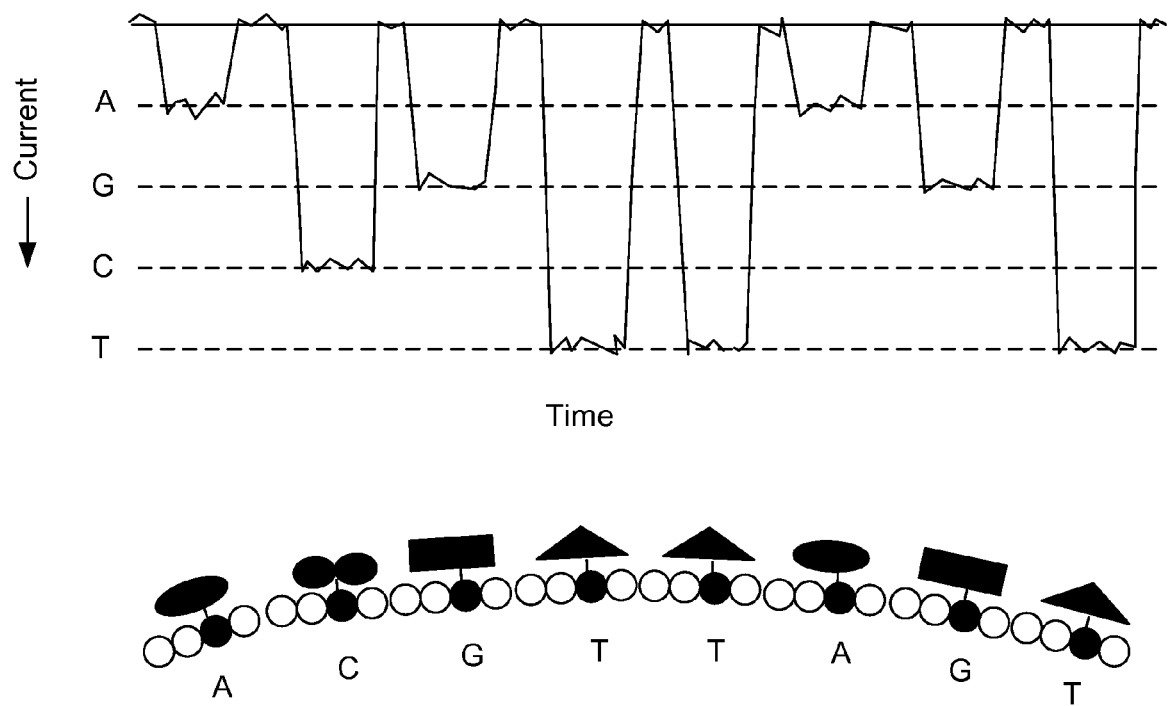
FIG. 4 illustrates how analog signals can be decoded into digital information that corresponds to the genetic sequence information encoded in an S-polymer.

FIG. 4 illustrates how the nanopore current signal is used to discriminate the different reporter constructs and determine the base identity of every fourth base along the S-polymer. In this case each reporter construct type blocks the baseline current signal to a different level, each level corresponding to a different base. An algorithm translates the current levels into base identities, sequentially in time, to produce the sequence A, C, G, T, T, A, G, T. This is the sequence of every fourth base along the S-polymer and by complementary base pairing with the DNA target template, it infers the corresponding sequence of every fourth base of the template is T, G, C, A, A, T, C, A.

Reporter constructs as depicted in FIG. 4 are designed to produce different nanopore current blocking signals. Other classes of reporter constructs can be designed for a broad range of high throughput and accurate detection technologies such as FRET, enzymatic luminescence, and electron beam scatter, electron beam absorption, and the like. Such technologies might not otherwise be useful to sequence native nucleic acids because of limited resolution. Inefficiencies in the sequencing detection processes can be reduced by pre-purifying batches of S-polymers to eliminate incomplete or short reaction products. Methods for end-modifying synthesized S-polymers can be utilized for both purification and as a means of facilitating S-polymer presentation to the detector. Furthermore, the reading process is not constrained by limitation to capping, uncapping, nucleotide extension, labeling, or other concurrent processing methods.

Figure 5A:
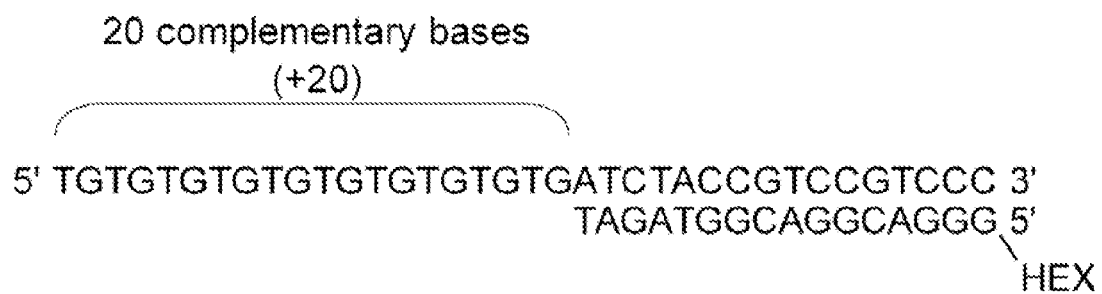
Figure 5B:
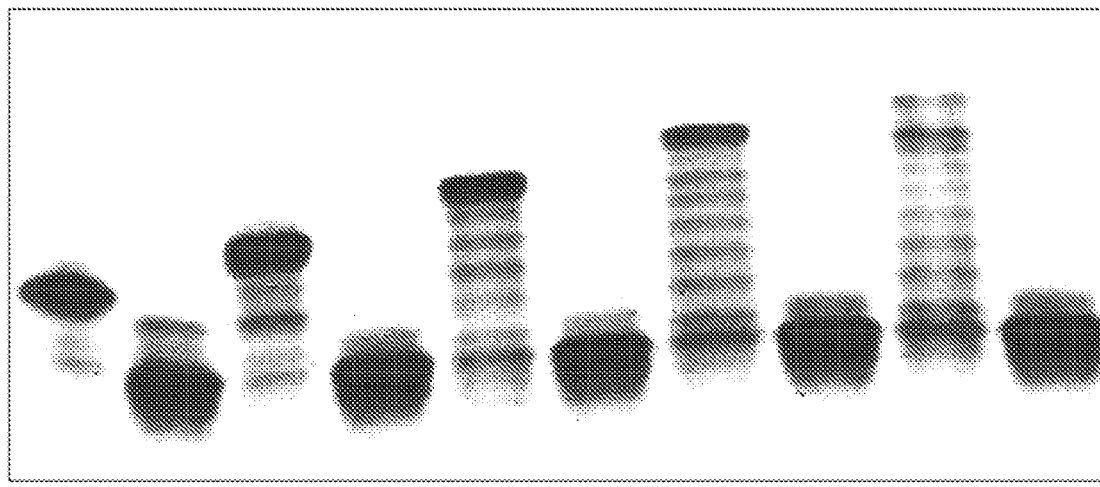
FIGS. 5B through 5G are gels of ligation products.

FIG. 5A describes a partial duplex template designed with a twenty base 5' overhang to demonstrate processive ligation of substrates and primer-initiated template-directed ligation in free solution. FIG. 5B is a photograph of a gel demonstrating ligation of the substrates using the primer-template format described in FIG. 5A. For this example, dinucleotide oligomeric substrates of the sequence 5' phosphate CA 3' are hybridized to the template in the presence of a primer and T4 DNA ligase. The unduplexed end-overhang (if any) is then nuclease digested and the ligation products are separated on a 20% acrylamide gel. The ligation results in product polymers containing demonstrably ligated subunits. As indicated by the banding pattern, the ligase positive reactions run out in lanes 1, 3, 5, 7 and 9, which contain progressively longer templates (4, 8, 12, 16, and 20 bases, respectively), demonstrate sequential ligation of 2 mer substrates (increased lengths of exonuclease protected duplexes). Lanes 2, 4, 6, 8 and 10 are negative controls containing no ligase and show complete exonuclease digestion of unligated products.

Figure 5C:
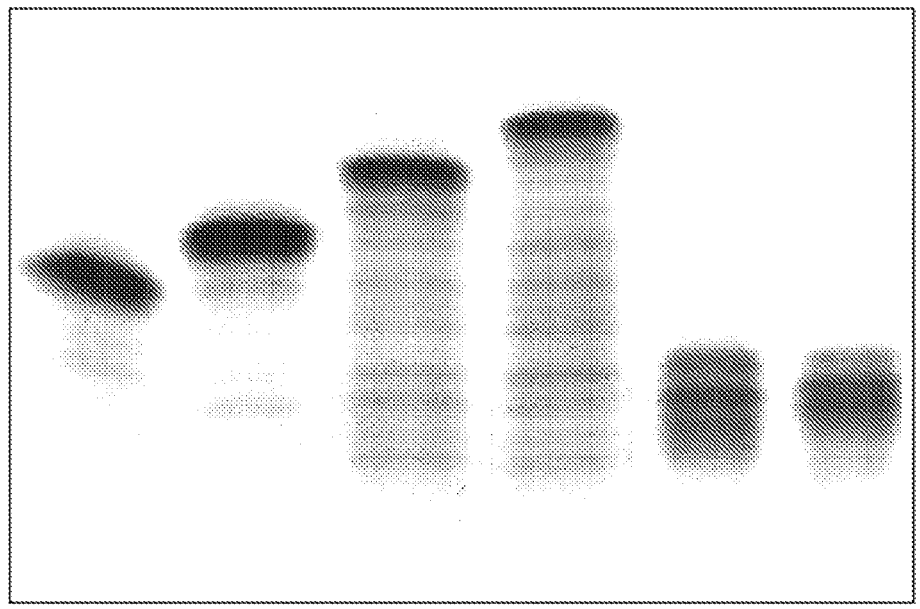

FIG. 5C is a second gel showing template-directed ligation of substrates. Four progressively longer positive control templates, again duplexed with an extension primer, were assayed (4, 8, 12, and 16 template bases, respectively). Again, dinucleotide oligomeric substrates of the sequence 5' phosphate CA 3' are hybridized to the template in the presence of a primer and T4 DNA ligase. The unduplexed end-overhang (if any) is then nuclease digested and the ligation products are separated on a 20% acrylamide gel. Oligomeric substrates (again 2 mers) are seen to ligate to the template in lanes 1, 2, 3 and 4, but not in lanes 5 and 6, where the template strands contain a mismatch with the 5' (phosphate) CA 3' dinucleotide (Lane 5 template-5' CGCG 3'; Lane 6 template-5' GGGG 3').

Figure 5D:
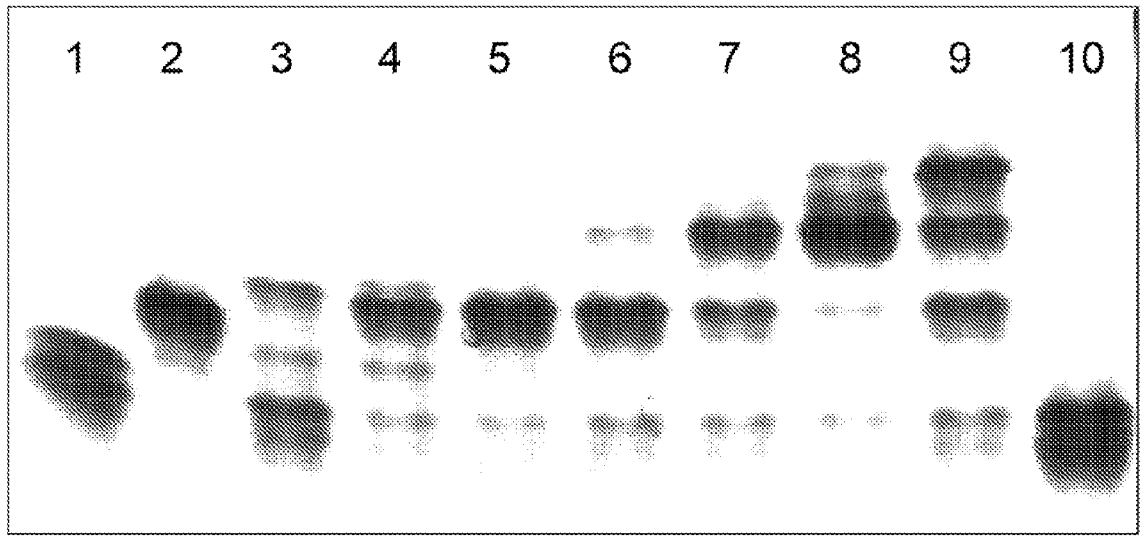

The gel results shown in FIG. 5D demonstrate multiple, template-directed ligations of a Bis(amino-modified) tetranucleotide probe. The aliphatic amino modifiers were of the linkage and composition described in FIG. 9A or 9B. For this example, a tetranucleotide oligomeric substrate of the sequence 5' (phosphate) C (amino) A (amino) C A 3' was hybridized to a range of progressively longer complementary templates (duplexed with an extension primer) in the presence of a primer and T4 DNA ligase. The unduplexed end-overhang (if any) was then nuclease digested and the ligation products are separated on a 20% acrylamide gel. The ligation results in product polymers containing demonstrably ligated subunits. Lanes 1 and 2 represent 16 mer and 20 mer size controls. Lanes 3, 4, 5, 6, 7, 8, and 9 show ligation products for progressively longer complementary templates (4, 6, 8, 12, 16, 18, and 20 template bases, respectively). Multiple tetramer ligations are observed for longer templates reactions (Lanes 6-9). Lane 10 shows essentially complete ligase inhibition due to template-probe mismatch (template—5' CGCG 3').

Figure 5E:
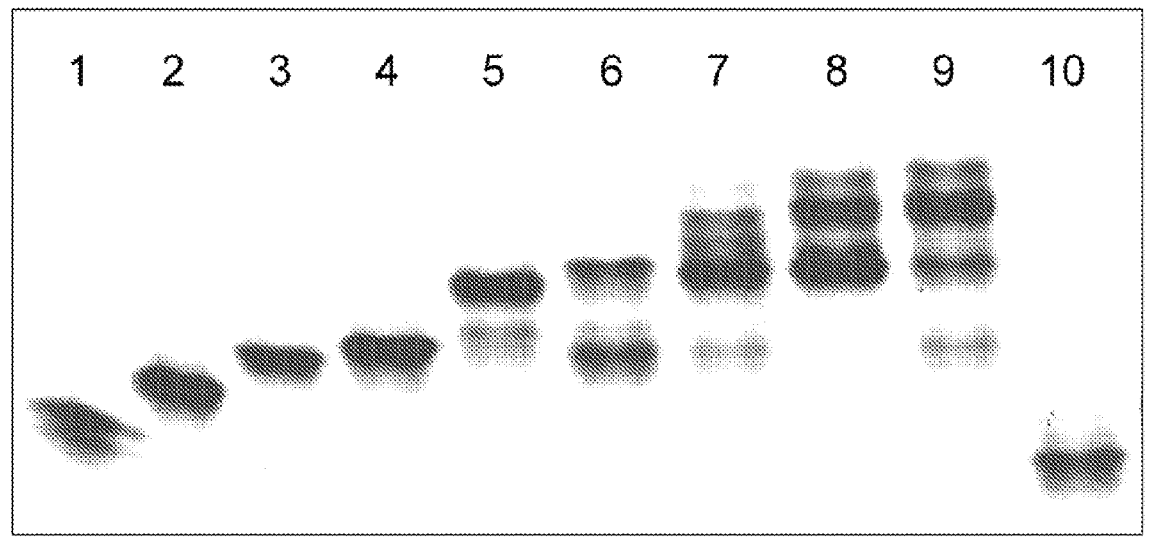

The gel results shown in FIG. 5E demonstrate multiple, template-directed ligations of a Bis(amino-modified) hexanucleotide probe. The aliphatic amino modifiers were of the linkage and composition described in FIG. 9A or 9B. For this example, a hexanucleotide oligomeric substrate of the sequence 5' (phosphate) C A (amino) C (amino) A C A 3' was hybridized to a range of progressively longer complementary templates (duplexed with an extension primer) in the presence of a primer and T4 DNA ligase. The unduplexed end-overhang (if any) was then nuclease digested and the ligation products are separated on a 20% acrylamide gel. The ligation results in product polymers containing demonstrably ligated subunits. Lanes 1 and 2 represent 16 mer and 20 mer size controls. Lanes 3, 4, 5, 6, 7, 8 and 9 show ligation products for progressively longer complementary templates (4, 6, 8, 12, 16, 18, and 20 template bases, respectively). Multiple hexamer ligations are observed for longer templates reactions (Lanes 5-9). Lane 10 shows nearly complete ligase inhibition due to template-probe mismatch (template—5' CGCGCG 3').

Figures 5F, 5G:
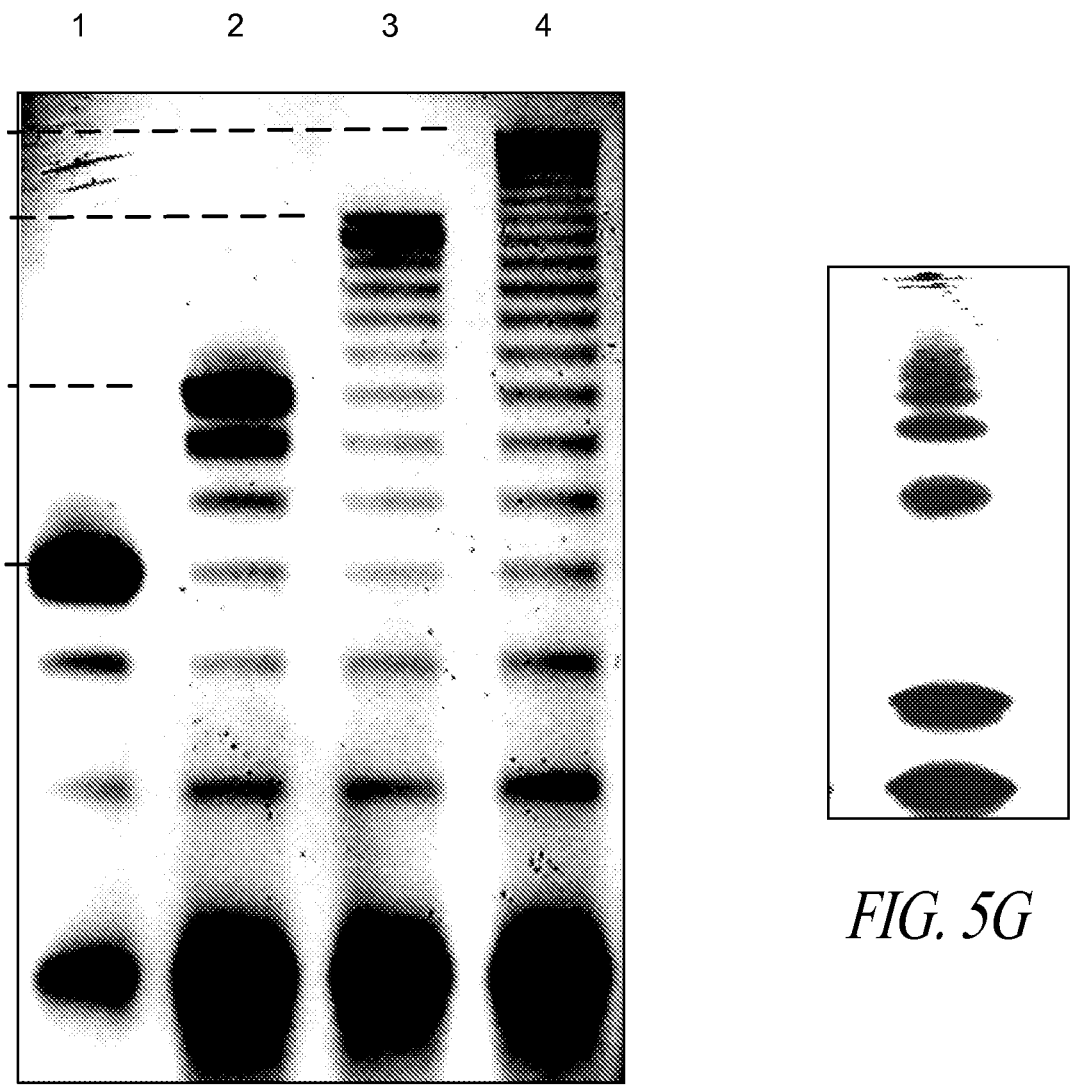

The gel results shown in FIG. 5F demonstrate multiple, template-directed ligations of a Bis(amino-modified) hexanucleotide probe. The aliphatic amino modifiers were of the linkage and composition described in FIG. 9A or 9B. For this example, the templates were fixed to magnetic beads and duplexed to a hex-labelled extension primer. Hexanucleotide oligomeric substrates of the sequence 5' (phosphate) C A (amino) C (amino) A C A 3' were hybridized to a range of progressively longer complementary templates in the presence of T4 DNA ligase, ligating and extending from the duplexed primer. The ligation product was then denatured from its template and separated on a 20% acrylamide gel. The ligation results in product polymers containing demonstrably ligated subunits. Ligation products in lanes 1 to 4 were produced on templates 18, 36, 68 and 100 bases in length. The upper rung in the ladder for each of the 4 lanes corresponds to ligated additions of 3, 6, 12 and 17 hexamers. These upper rungs are relatively strong bands and indicante that much longer ligation products will be possible.

Figure 6A:
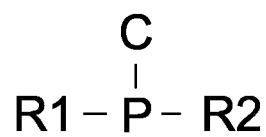
FIG. 6A illustrates structural components of S-mers.

The gel results shown in FIG. 5G demonstrate multiple, template-directed ligations of tetranucleotide probe modified with a PEG3500 attached at each end to two modified probe nucleotides. The probe precurser was a Bis 2,3 (amino)Tetranucleotide, 5' (phosphate) C A (amino) C (amino) A 3'. The aliphatic amino modifiers were of the linkage and composition described in FIG. 9 A or 9B and were then converted to 4-formylbenzoate (4FB). Bis (amino) PEG3500 converted to Bis (HyNic) PEG3500, (HyNic conjugation kit was purchased from Solulink, CA). Under dilute conditions the bifunctional PEG3500 was reacted with the Bis 2,3 (4FB) tetranucleotide to form a circularized PEG loop. As in the previous example, a template was fixed to magnetic beads and duplexed to a hex-labelled extension primer. In this example, template is 20 bases long. The PEG-circularized tetranucleotide probes were hybridized to the complementary template in the presence of T4 DNA ligase, ligating and extending from the duplexed primer. The ligation product was then separated from its template and separated on a 20% acrylamide gel. The ligation results in product polymer containing 4 PEG-modified probes. This demonstrates that doubly modified probes loaded with mass of high masses of 3500 Daltons can be progressively ligated to a template. FIG. 6A shows a component illustration of the S-mer (also referred to as a construct) where P represents the probe, C represents the reporter construct and R1 and R2 represent linkage groups on each end of the probe. As discussed previously, the probe and reporter construct may be different moieties, or the probe itself may have properties whereby it functions as the reporter construct.

R1 and R2 may be the same or different and are independently hydroxyl, hydrogen, triphosphate, monophosphate or amine, or are an ester, an ether, a glycol, an amide, or a thioester. The R1 and R2 end groups are configured as appropriate for the synthesis protocol in which the S-mer is used. For example, R1=5'-phosphate and R2=3'-OH, would find use in a ligation protocol, while R1=5'-triphosphate and R2=3'-OH would be suitable for a polymerase protocol. Optionally, R2 can be configured with a reversible blocking group for cyclical single-substrate addition. Alternatively, R1 and R2 can be configured with linker end groups for chemical coupling, or with no linker groups for a hybridization only protocol. R1 and R2 can be of the general type XR, wherein X is a linking group and R is a functional group.

The S-mers are reagent precursors to the S-polymer and are generally comprised of a probe member and a reporter construct. The probe is an oligomer substrate, generally made up of a plurality of nucleobase residues. By generating combinatorial-type libraries of two to twenty nucleobase residues per probe, generally 2 to 10 and typically 2, 3, 4, 5 or 6 nucleobase residues per probe, probe polymer libraries useful as reagents in the synthesis of S-mers are generated.

The S-mer probes are used for template-dependent assembly of an S-polymer. The motifs have species-specific variability. Each particular subunit in the daughter strand is selected from a library of motifs by a template-directed process and its probe binds to a corresponding sequence of complementary nucleotides on the template strand. In this way, the sequence of nucleobase residues of the probes forms a contiguous, complementary copy of the target template strand.

Figure 6B:
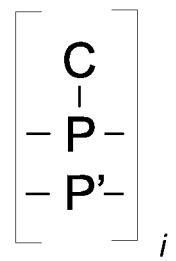
FIGS. 6B and 6C illustrate the subunits of a duplexed and non-duplexed S-polymer, respectively.
Figure 6C:
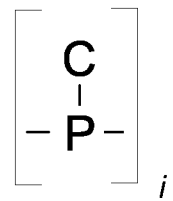

FIG. 6B shows the $i^{th}$ subunit of a duplex S-polymer, wherein i denotes a chain of m subunits, where i=1, 2, . . . to m, where m>10, generally m>30, and typically m>100 or m>1000. This subunit includes the S-mer after incorporation, depicted by P and C portions along with the portion of the target template to which the S-mer probe had a complementary match, depicted by P'. FIG. 6C shows the subunit of the single stranded S-polymer after the template target is separated by denaturing. As mentioned above, denaturation is optional if the duplex (FIG. 6B) is measured directly.

Brackets in FIGS. 6B and 6C indicate a subunit of the polymer product, wherein each subunit is a subunit motif having a species-specific probe member, further wherein said probe members P, of said subunit motifs are serially complementary to the corresponding contiguous nucleotide sequence of the template strand portion P', and form a primary backbone of the S-polymer. The reporter constructs will encode for a portion of the nucleotide sequence within P (and through complementarity a portion of P'). This encoded information is used to determine one or more bases at certain positions within the length of the probe.

In some embodiments, S-mers have linkages for reporter constructs to be attached or completed after S-polymers have been assembled. Multiple linkage species may attach to species specific reporters to preserve base information or the base information may be encoded by numbers of linkages and be determined by reporter density. Linker groups can be chosen from a broad range of suitable commercially available chemistries (Pierce, Thermo Fisher Scientific, USA) and can be adapted for this purpose. Common linker chemistries include, for example, NHS-esters with amines, maleimides with sulfhydryls, imidoesters with amines, EDC with carboxyls for reactions with amines, pyridyl disulfides with sulfhydryls, and the like. Other embodiments involve the use of functional groups like hydrazide (HZ) and 4-formylbenzoate (4FB) which can then be further reacted to form linkages. More specifically, a wide range of crosslinkers (hetero- and homobifunctional) are broadly available (Pierce) which include, but are not limited to, Sulfo-SMCC (Sulfosuccinimidyl 4-[N-maleimidomethyl]cyclohexane-1-carboxylate), SIA (N-Succinimidyl iodoacetate), Sulfo-EMCS ([N-e-Maleimidocaproyloxy]sulfosuccinimide ester), Sulfo-GMBS (N-[g-Maleimido butyryloxy]sulfosuccinimide ester), AMAS N-(a-Maleimidoacetoxy)succinimide ester), BMPS(N EMCA (N-e-Maleimidocaproic acid)-[β-Maleimidopropyloxy]succinimide ester), EDC (1-Ethyl-3-[3-dimethylaminopropyl] carbodiimide Hydrochloride), SANPAH(N-Succinimidyl-6-[4'-azido-2'-nitrophenylamino]hexanoate), SADP (N-Succinimidyl(4-azidophenyl)-1,3'-dithiopropionate), PMPI (N-[p-Maleimidophenyl]isocy, BMPH(N-[β-Maleimidopropionic acid]hydrazide,trifluoroacetic acid salt)anate), EMCH ([N-e-Maleimidocaproic acid]hydrazide, trifluoroacetic acid salt), SANH (succinimidyl 4-hydrazinonicotinate acetone hydrazone), SHTH (succinimidyl 4-hydrazidoterephthalate hydrochloride), and C6-SFB (C6-succinimidyl 4-formylbenzoate). Also, the method disclosed by Letsinger et al. ("Phosphorothioate oligonucleotides having modified internucleoside linkages", U.S. Pat. No. 6,242,589) can be adapted to form phosphorothiolate linkages.

Another alternative method to species specific linking of reporters discussed above is to use species-specific sequential protection/deprotection chemistries to attach the correct reporters. Well established protection/deprotection chemistries are broadly available for common linker moieties (Benoiton, "Chemistry of Peptide Synthesis", CRC Press, 2005). Amino protection include, but are not limited to, 9-Fluorenylmethyl carbamate (Fmoc-NRR'), t-Butyl carbamate (Boc-NRR'), Benzyl carbamate (Z-NRR', Cbz-NRR'), Acetamide Trifluoroacetamide, Phthalimide, Benzylamine (Bn-NRR'), Triphenylmethylamine (Tr-NRR'), and Benzylideneamine p-Toluenesulfonamide (Ts-NRR'). Carboxylprotection include, but are not limited to, Methyl ester, t-Butyl ester, Benzyl ester, S-t-Butyl ester, and 2-Alkyl-1,3-oxazoline. Carbonyl include, but are not limited to, Dimethyl acetal 1,3-Dioxane, and 1,3-Dithiane N,N-Dimethylhydrazone. Hydroxyl protection include, but are not limited to, Methoxymethyl ether (MOM-OR), Tetrahydropyranyl ether (THP-OR), t-Butyl ether, Allyl ether, Benzyl ether (Bn-OR), t-Butyldimethylsilyl ether (TBDMS-OR), t-Butyldiphenylsilyl ether (TBDPS-OR), Acetic acid ester, Pivalic acid ester, and Benzoic acid ester.

While the reporter construct is often depicted as having a single tether linkage to the probe, it may have multiple tethers or may be incorporated into the probe itself. The reporter construct can comprise a scaffold to which one or more reporters are linked. Some methods of encoding information include arranging the reporters to provide shape or dimensionality that can be detected, varying numbers of reporters in a continuous or discrete manner, varying types of reporters or using a combination of methods. Reporter linkages can comprise one or different chemistries to attach one or more different three reporter groups so that reporters can be attached after the S-polymer backbone has been assembled.

Depending upon the requirements of the detection process, S-polymers may be measured in the duplex form. Alternatively they may be denatured into the single strand form. Methods for dissociation of the template strand include heat denaturation or chemical degradation. The S-polymer product strand contains a plurality of subunits i, where i denotes the $i^{th}$ subunit in a chain of m subunits making up the daughter strand, where i=1, 2, 3 to m, where m>10, m>30, m>100, or m>1000.

In another embodiment, polymerase-based methods are disclosed for assembling product S-polymers. In this case, the end groups R1 and R2 of the S-mers are chosen to be 5'-triphosphate and 3'-OH as appropriate for reactions involving a polymerase. Generally, polymerase substrates are mononucleotides, but polymerase can also incorporate dinucleotide, trinucleotide, and tetranucleotide triphosphate oligonucleotides with a level of efficiency and fidelity in a primer-dependent, processive process as disclosed by Kless in U.S. Pat. No. 7,060,440. The selection of a suitable polymerase is part of a process of optimizing the experimental protocol.

Figure 7:
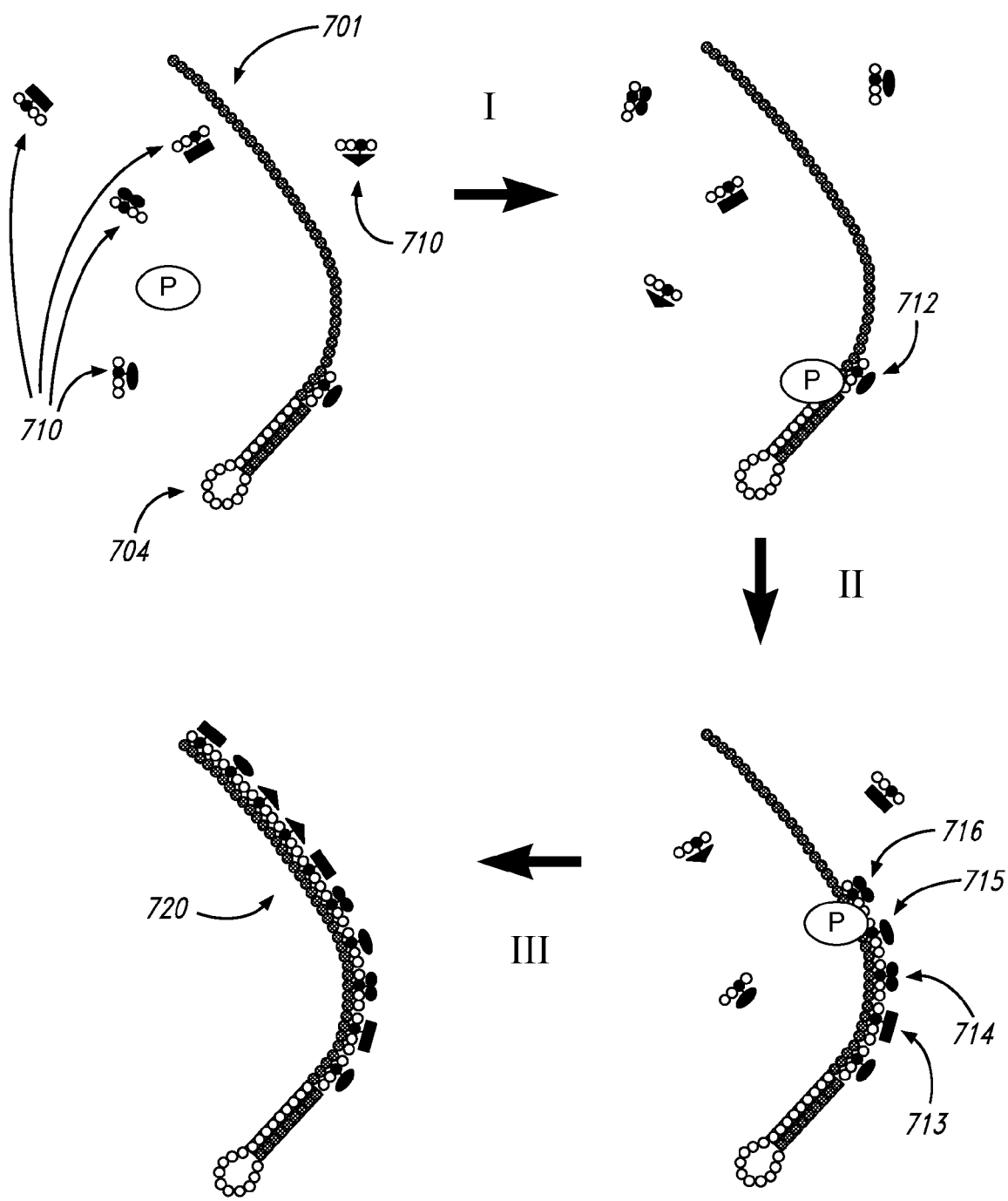
FIG. 7 illustrates simplified steps for synthesizing an S-polymer from a target nucleic acid using polymerase.

In the example depicted in FIG. 7, a primed template strand (701) has been prepared by end adapting with a universal hairpin primer (704). A reaction mixture that contains the primed template strand is contacted with a library of S-mers (710) and a polymerase (P), under conditions optimized for template-directed polymerization. Here, In Step I, the polymerase begins to processively add S-mers to the template strand, as depicted by S-mer (712). This process continues in Steps II and III, as depicted by the addition of S-mers (713, 714,715,716). Each probe subunit (S-mer) added is a particular species selected by specific binding to the next adjacent oligomer of the template so as to form a contiguous complementary copy of the template. While not bound by theory, the polymerase is thought to assist in ensuring that incoming probe species added to the nascent chain are specifically complementary to the next available contiguous segment of the template. Loeb and Patel describe mutant DNA polymerases with increased activity and improved fidelity (U.S. Pat. No. 6,329,178). Williams, for example, in U.S. Patent Application 2007/0048748 has shown that polymerases can be modified for increased speed of incorporation and reduction in error rate, clearly linking error rate not with hybridization accuracy but rather with polymerase processivity. Step III results in a completed duplex S-polymer (720).

In this embodiment, S-mers are polymerized processively, the extension, crosslinking, end activation, and high stringency washing steps typically associated with cyclical sequencing by synthesis methods are optionally eliminated with this approach. Thus the reaction can be performed in solution. S-polymer synthesis with S-mers can also be performed with immobilized templates (on solid substrates, in porous gels, and the like), for purposes of genome template parsing to help post-assembly, secondary structure reduction, purification, in process reagent modification or other. Further, methods for stretching the template to relief secondary structure are readily adapted to S-polymer synthesis.

Polymerases include, but are to limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tli DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

An analagous alternative to enzymatic ligation is chemical ligation. A chemical ligation of S-mers to form S-polymers uses chemical functional groups for the R1 and R2 end groups of the S-mer that are selectively reactive. Under appropriate conditions, S-mers that are abutted and stabilized for some minimal time by template-dependent hybridization on the target DNA will couple. Coupling chemistries for this method of chemical coupling are known to someone skilled in the art and include, for example, the techniques disclosed in U.S. Pat. No. 6,951,720 to Burgin et al. Methods of chemical ligation of probes are described in patent application No. PCT/US2008/067507 as it applies to template dependent synthesis of a polymer product using Xprobes or Xmers. These methods are readily adapted to synthesis of the S-polymer product using S-mers.

Further description of different implementations of enzymatic polymerase, enzymatic ligation and chemical ligation methods are also described in patent application No. PCT/US2008/067507. These are readily adapted for use in S-polymer synthesis using S-mers. Variations of the methods that can be adapted include both solid substrate and free solution methods of synthesis, priming methods, and nonprimed synthesis methods ("promiscuous ligation"). Other auxiliary techniques such as methods to reduce secondary structure can be adapted from this reference.

An overview of synthetic techniques is presented below, beginning with probe end groups, probe oligomers and finally reporter constructs. As previously described S-mers are oligonucleotide probes with end groups R1 and R2 appropriately adapted for enzymatic polymerization, enzymatic ligation or chemical ligation.

Tether modified oligonucleotide triphosphates of length n (n=2, 3, 4 . . . 20) can be used as substrates for polymerase-based incorporation into S-polymers. A variety of methods can be employed for robust synthesis of 5' triphosphate S-mers. As described by Burgess and Cook ("Syntheses of Nucleoside Triphosphates", *Chem. Rev.* 100(6):2047-2060, 2000), these methods include but are not limited to reactions using nucleoside phosphoramidites, synthesis via nucleophilic attack of pyrophosphate on activated nucleoside monophosphates, synthesis via nucleophilic attack of phosphate on activated nucleoside pyrophosphate, synthesis via nucleophilic attack of diphosphate on activated phosphate synthon, synthesis involving activated phosphites or phosphoramidites derived from nucleosides, synthesis involving direct displacement of 5'-O-leaving groups by triphosphate nucleophiles, and biocatalytic methods. A representative method for producing polymerase compatible dinucleotide substrates uses N-methylimidazole to activate the 5' monophosphate group; subsequent reaction with pyrophosphate (tributylammonium salt) produces the triphosphate (Abramova et al., "A facile and effective synthesis of dinucleotide 5'-triphosphates", *Bioorganic and Med. Chem*, 15, 6549-6555, 2007).

The SSP method assembles a replica of the target nucleic acid that accurately complements the encoded base and maintains base-to-base spacing along the target length by a template-directed synthesis, generally a process or combination of processes selected from hybridizing, ligating, polymerizing, and chemically crosslinking of S-mers. S-mers are supplied as reagent libraries (e.g., as parts of kits for sequencing) for this purpose. The libraries are generally combinatorial in nature, and contain probe members selected to specifically bind to any or all of the complementary sequences such as would be found in a target polynucleotide. The number of probes required in a library for this purpose is a function of probe size and the type of nucleobases incorporated. Each probe can complement to one or more sequence fragments in the template, and a sufficient variety of probe members must be present to form a contiguous complement to the sequence fragments of the target polynucleotide. Using standard bases A, T, C and G, probes which are dimers have 16 possible species combinations, probes which are trimers have 64 possible species, and so forth. S-mers only encode for a portion of the probe base information and can use universal bases for those bases that are not encoded for. Universal bases form "base pairs" with each of the natural DNA/RNA bases with little discrimination between them (Loakes, D., "Survey and Summary: The applications of universal DNA base analogues," *Nucleic Acids Research* 29(12): 2437-2447, 2001). Use of the universal bases reduces the library size accordingly. For example, a tetramer probe that encodes only for the 5' end base could be designed using natural bases for the 5' end position and universal bases in the other 3 positions reducing the library size to 4 from 64. S-mers only require high fidelity matching for the base pairs for which the S-mer encodes information. Enzymatic base checking characteristics can be beneficial for this application because of their localized activity. For example, ligase will ligate only matched bases with high efficiency in its active site. Enzymatic ligation of long probes, that may include universal bases, will depend upon only the fidelity of one or a few bases in the vicinity of its active region. If the bases used for encoding are positioned in the ligase active site, only high fidelity matched S-mer probes will be incorporated into the S-polymer. For smaller S-mer probe sizes up to ~8 bases long, use of conventional bases can lead to reasonable sized libraries. Larger S-mer probes may require the use of universal bases to keep the library sizes small enough for kinetic and critical density reasons.

The probe portion of the S-mer is a modified oligonucleobase having a chain of X deoxyribonucleotides, ribonucleotides, or more generally, nucleobase residues (where x can 2, 3, 4, 5, 6, or more). In these discussions a probe with 2, 3, 4, 5 or 6 nucleobase residues in length can be referred to as a 2 mer, 3 mer, 4 mer, 5 mer, or 6 mer, respectively.

Figure 8:
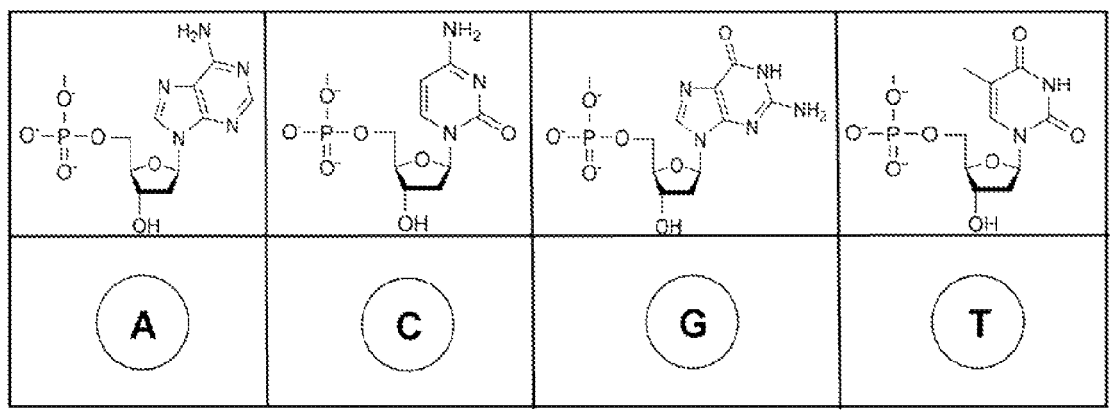
FIG. 8 illustrates structures of deoxyadenosine (A), deoxycytosine (C), deoxyguanosine (G), and deoxythymidine (T).

S-mer reagents can be synthesized with an oligonucleotide 5'-3' phosphodiester backbone, the probe having the nucleotides A, T, G and C (structures shown in the table of FIG. 8), or other hybridizable nucleic acid analogs such as those having a peptide backbone, phosphono-peptide backbone, serine backbone, hydroxyproline backbone, mixed peptide-phosphono-peptide backbone, mixed peptide-hydroxyproline backbone, mixed hydroxyproline-phosphono-peptide backbone, mixed serine-phosphono-peptide backbone, threose backbone, glycol backbone, morpholino-backbone, and the like, as are known in the art. Deoxyribonucleic acid oligomers and ribonucleic acid oligomers, and mixed oligomers of the two, may also be used as probes. Other bases may also be substituted, such as uracil for thymidine, and inosine as a degenerate base. Fragmentary residues of nucleobases having complementarity can also be used. Other universal, degenerate and/or wobbly bases known in the art that can be used include, but are not limited to, xanthine, hypoxanthine, or a heterocyclic derivative, analog, or tautomer of xanthine and hypoxanthine, 8-azapurine, purines substituted at the 8 position with methyl- or bromo-, 9-oxo-$N^6$-methyladenine, 2-aminoadenine, 7-deazaxanthine, 7-deazaguanine, 7-deazaadenine, $N^4$-ethanocytosine, 2,6-diaminopurine, $N^6$-ethano-2,6-diaminopurine, 5-methylcytosine, 5-($C_3$-$C_6$)-alkynylcytosine, 5-fluorouracil, 5-bromouracil, thiouracil, 2-hydroxy-5-methyl-4-triazolopyridine, isocytosine, pseudoisocytosine, isoguanine, 7,8-dimethylalloxazine, 6-dihydrothymine, 5,6-dihydrouracil, 4-methyl-indole, ethenoadenine and the nucleobases described in U.S. Pat. Nos. 5,432,272 and 6,150,510, published PCTs WO 92/002258, WO 93/10820, WO 94/22892, and WO 94/22144, and in Fasman, Practical Handbook of Biochemistry and Molecular Biology, pp. 385-394, CRC Press, Boca Raton, La., 1989.

There are alternative designs for the reporter construct. One design has the reporter construct embedded in the probe itself. In this case the reporter characteristic that encodes the base information (and is detected) is integral to the probe. An example of this is described above, where the S-mer probe has 4 bases, the 5' end base being either A, C, T or G and the remaining 3 being universal bases. In this case, the base itself conveys the information and the universal bases provide spacing with which to detect it. An example detection method that would benefit from the S-polymers of such S-mer probes would be tranverse tunneling in a nanopore where confounding base-to-base variations would be reduced. Another reporter construct example is a variation on the last example whereby a different universal base could be used for each of A, C, T or G. In this case each universal base type is chosen so it has some feature that further discriminates it from the other bases, such as size, electron density, shape or capacitance. In this reporter construct design type, enzymatic methods of template-dependent S-polymer synthesis require that the probe (and integral reporter construct) be recognized as a substrate.

In another reporter construct design type, the reporter construct is attached to the probe by one or more tether(s). This is advantageous because the enzyme need only recognize the probe substrate and not be sterically inhibited, thus providing more reporter design flexibility. The following synthesis methods describe this type of reporter construct design. Generally an S-mer has a single reporter construct with a single tether attaching to the probe, but it should be understood that multiple reporter constructs on one or each with one or more tethers attached to the probe are simple extensions within the scope of this invention. These variations may have further benefits such as stabilizing the reporter construct body orientation with respect to the probe or providing more efficient multiplexed encoding.

Figure 9A:
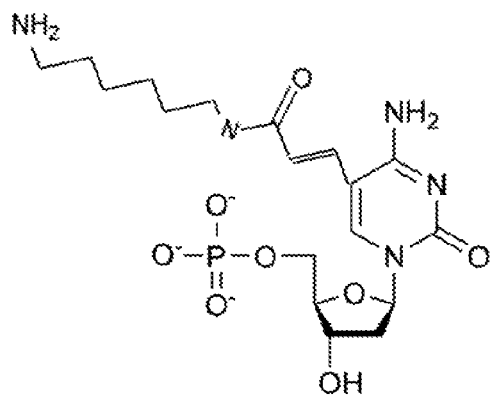
FIGS. 9A and 9B illustrate nucleotides derivatized with functional groups.
Figure 9B:
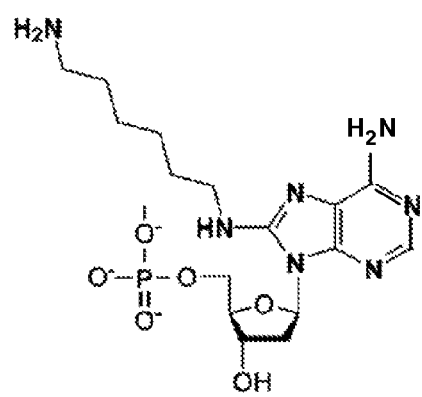

As is known in the art, oligomers can be designed to include nucleotide modifiers. In some embodiments, these serve as the attachment point for the reporter construct tether. Purine and pyrimidine derivatives suitable for synthesis of derivatized oligomers are well known in the art. Two such representative modified bases are shown in FIGS. 9A and 9B, wherein a 5-amino-modified cytosine derivative and an 8-amino-modified guanine residue are depicted.

Figure 10A:
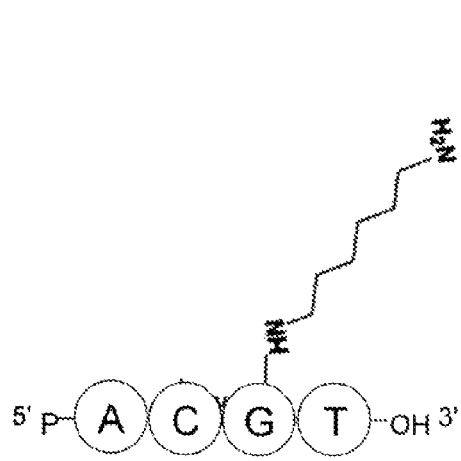
FIGS. 10A and 10B illustrate probes incorporating derivatized nucleobases.
Figure 10B:
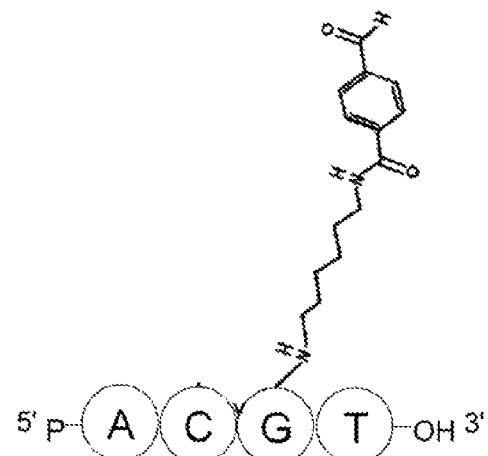

As illustrated in FIGS. 10A and 10B, taking a 4 mer probe as an example (here illustrated as 5'-monophosphate), any of the four base positions on the oligomer can be modified to create a tether attachment point by known chemistries. A modified nucleotide at probe residue 2 is illustrated in FIG. 10A. This figure illustrates a 4 mer oligomer with an amino linker attached to the guanine of the probe. FIG. 10B illustrates a 4 mer probe with a benzaldehyde functional group attached to the guanine. Synthesis of these linkers can proceed using Amino-Modifier C6 phosphoramidites, that are commercially available for all four nucleotides (Glen Research, USA). An alternative linker such as the benzaldehyde modified nucleotides can be developed by further phosphoramidite modification or post-oligo-assembly linker modification. HPLC or other size and/or affinity purification is useful to enrich for correctly assembled S-mers.

The details are illustrative of methods well known in the art. For simplicity, most illustrations provided herein will assume 4 mers unless otherwise noted, but it is understood that other S-mer libraries or library combinations may be employed in the practice of this invention.

In other embodiments, the phosphodiester backbone of the substrate can be modified to create attachment points for the tether as disclosed by Cook et al. ("Oligonucleotides with novel, cationic backbone substituents: aminoethylphosphonates", *Nucleic Acids Research* 22(24): 5416-5424, 1994), Agrawal et al. ("Site specific functionalization of oligonucleotides for attaching two different reporter groups", *Nucleic Acids Research* 18(18): 5419-5423, 1990), De Mesmaeker et al. ("Amide backbone modifications for antisense oligonucleotides carrying potential intercalating substituents: Influence on the thermodynamic stability of the corresponding duplexes with RNA- and DNA-complements", *Bioorganic & Medicinal Chemistry Letters* 7(14): 1869-1874, 1997), Shaw et al. (Boranophosphates as mimics of natural phosphodiesters in DNA", *Curr Med. Chem.* 8(10):1147-55, 2001), Cook et al. (U.S. Pat. No. 5,378,825), and Agrawal ("Functionalization of Oligonucleotides with Amino Groups and Attachment of Amino Specific Reporter Groups", *Methods in Molecular Biology*, Vol. 26, 1994). The nucleobase residues making up the probe member can be substituted with nucleobase analogs to alter S-mer functionality. For example, Locked Nucleic Acids ("LNA") can be used to increase probe duplex stability. If chemical coupling of S-mer is intended (instead of enzymatic ligation), probe 5' and 3' ends can be further derivatized to allow for chemical crosslinking.

A reporter construct and its tether may be made by a variety of polymer chemistries, and its use and synthesis is discussed in more detail here. Reporter constructs are physical manifestations of reporter codes, which are bioinformational and digital in nature. Reporter codes encode the genetic information associated with the probe or nucleobase sequence fragment to which the reporter construct and its tether is attached. By design, only partial sequence information is encoded to provide space both for larger reporter structures and to reduce resolution requirements of the detector. The reporter constructs are designed to optimize the detectability of the reporter code by adjusting spatial separations, abundance, and signal strength of the constituent reporters. In general there is a single reporter construct with a single signaling entity but multiple spatially separated reporter constructs on one S-mer could be designed. The tether must be long enough to not inhibit enzyme activity, but should be short enough so that adjacent reporter constructs overlap is minimized. The reporter constructs can incorporate a broad range of signal and structural elements including, but not limited to, polymers, dendrimers, beads, aptamers, ligands, oligomers, branched polymers, nanoparticles, and nanocrystals, as well as reporter chemistries and reporters to be detected with the appropriate detection technology. Base-specific labels can be introduced (via attachment to the reporter construct) either prior to or after S-polymer backbone assembly, by covalent or by affinity-directed binding. These reporter constructs are made by a variety of polymer chemistries and are discussed further below.

In one embodiment, the reporter constructs are attached to the probe or nucleobase with a polymer tether. The tethers can be constructed of one or more durable, aqueous- or solvent-soluble polymers including, but not limited to, the following segment or segments: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, sidechain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments. Such polymers can be circularized at two attachment points on a S-mer to further constrain the reporter construct.

Figure 11A:
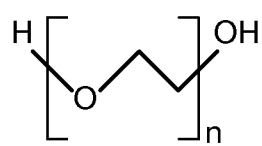
FIGS. 11A through 11B illustrates PEG polymer subunit and use of PEG as a polymeric tether.
Figure 11B:
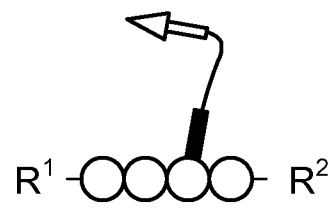

Polyethylene glycol (PEG), polyethylene oxide (PEO), methoxypolyethylene glycol (mPEG), and a wide variety of similarly constructed PEG derivatives (PEGs) are broadly available polymers that can be utilized in the practice of this invention. Modified PEGs are available with a variety of bifunctional and heterobifunctional end crosslinkers and are synthesized in a broad range of lengths. PEGs are generally soluble in water, methanol, benzene, dichloromethane, and many common organic solvents. PEGs are generally flexible polymers that typically do not non-specifically interact with biological chemicals. FIG. 11A shows the structure of PEG and FIG. 11B illustrates a PEG tether linked to the probe at one end (indicated by the black block) and has a linker for attaching a reporter or reporter construct at the other end (indicated by the arrow).

Other polymers that may be employed as tethers, and provide "scaffolding" for reporters, include, for example, polyglycine, poly-proline, poly-hydroxyproline, poly-cysteine, poly-serine, poly-aspartic acid, poly-glutamic acid, and the like. Side chain functionalities can be used to build functional group-rich scaffolds for added signal capacity or complexity.

Figure 12A:
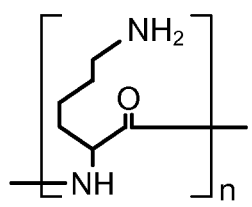
FIGS. 12A and 12B illustrate poly-lysine polymer subunit and use of poly-lysine as a reporter scaffold.

FIG. 12A shows the structure of poly-lysine. In the reporter construct illustrated in FIG. 12B, the poly-lysine tether segments create a scaffolding for reporter attachment and the ε-amino groups of the lysine side chains (indicated by arrows) provide functionality for attachment of pluralities of reporter elements to a S-mer. FIG. 12C is a schematic to illustrate a branched scaffold (reporter attachment points are indicated by arrows) such as a starburst dendrimer.

Given the flexibility of the SSP approach, a broad range of reporters are used to produce unique, measurable signals. The reporter construct scaffolding to which the reporter moieties are attached can be constructed using a broad range of existing structural features including, but not limited to dendrimers, beads, polymers, and nanoparticles. Depending on the coding scheme, one or many distinctly separated reporter scaffolds can be used for the reporter code of each tether. Any number of options are available for direct and indirect attachment of reporter moieties to the reporter scaffolding, including (but not limited to): reporter coding of chemically reactive polymer(s) integrated into the tether constructs; reporter coding of chemically reactive surface groups on dendrimer(s) integrated into the tether backbone; and reporter coding of chemically reactive surface groups on bead(s) attached to the tether. In this context, a "bead" is taken broadly to indicate any crystalline, polymeric, latex, or composite particle or microsphere.

Following purification of the reporter construct itself to remove incomplete or broken reaction product, the construct can be directly coupled to the probe via its linker. As with all methods of polymer synthesis, purification (size, affinity, HPLC, electrophoresis, etc.) is utilized following completion of S-mer synthesis and assembly to ensure high purity viable product.

Reducing the size and mass of the S-mer can also be achieved by using unlabeled tethers. By eliminating bulky reporters (and reporter scaffolding such as dendrimers, which for some encoding embodiments comprise over 90% of the tether mass), hybridization and/or coupling kinetics can be enhanced. Post-assembly tether labeling can then be employed. Reporters are bound to one or more linkage chemistries that are place on the tether to encode the base sequence information. In one embodiment, chemistries are placed on the tethers in 4 possible states and are used in an S-mer library to identify four encoded base types. After the S-polymer has been assembled, reporters are attached that will convey the encoded base information.

A number of strategies can be employed for physically representing the encoded base information but practical limitations must be considered. S-polymers are a serial concatenation of S-mers, where each S-mer carries a reporter construct. This means the detection method used to read the S-polymers must at least be able to resolve reporter constructs that are separated the length of the S-mer, S. This further implies the size of the reporter construct itself will generally have a size equal to or less than S.

Generally S-mers will encode for 1 base. Encoding for more or less information such as 2 bases or 1 bit is also possible. An example of 1 bit of base information are the 2 states: (A or C), (T or G). Generally a single reporter construct has a single spatially resolvable signal. To encode for 1 base type A, C, T, or G in a single spatially resolvable signal, requires least 4 states. Many different reporter constructs can encode 4 states. Several different examples are described along with associated detection technologies below.

The S-polymer can be labeled and measured by any number of techniques. The massive data output potential of the SSP method is well matched to nanopore detection arrays or other nanometer-resolution technologies.

Nanopore detection is based the Coulter counting method. FIG. 13 illustrates a S-polymer being threaded through a synthetic nanopore. The nanopore is 2 to 15 nm in diameter and is 1 to 10 nm long. Two reservoirs, A and B, are filled with a conductive solution that has high concentrations of electrolyte, (typically 1M KCl) and are fluidically and thereby conductively connected by the nanopore. By applying a potential between the reservoirs, a current passes through the nanopore and any molecular constructs within the nanopore modulate the current. Furthermore, the applied potential can drive the molecular construct through the nanopore by electrophoresis or electroosmotic means. S-polymers reporter constructs can be threaded through the nanopore and measured in this way. The portion of the S-polymer segment residing in the nanopore channel produces the different current signatures. To achieve good resolution of the reporter constructs must be close to the same length or longer than the nanopore. The amount and distribution of charged polymer residing in the nanopore modulates both the electrolyte species current and the translocation velocity.

One embodiment is to have the average charge density of the S-polymer designed to be similar to that of native DNA. In this case the negatively charged S-polymers are added to the reservoir A solution. In this example, the reporter constructs are designed to produce 5 levels of impedance resulting in 5 current levels measured in the nanopore detector. These include a baseline level due to the S-polymer backbone alone and 4 levels caused by each of 4 different reporter constructs on the S-polymer backbone. As the S-polymer is threaded through the nanopore, each reporter construct blocks current at a certain level corresponding to the encoded base information. FIG. 4 is an illustration of this output.

Figure 12B:
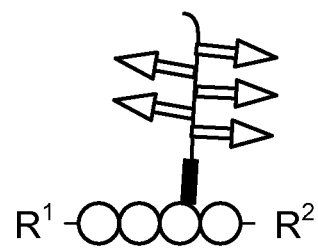
Figure 12C:
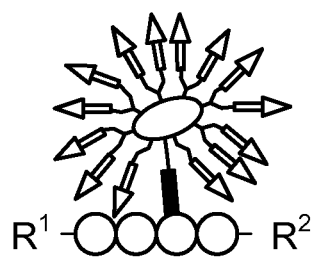
FIG. 12C illustrates the use of a tethered dendrimer as a reporter scaffold.

The four reporter constructs can be designed using a polylysine scaffold of type illustrated in FIG. 12B that couples to linear peptides of 4 different lengths. The coupled peptides, such as polyglutamic acid, are the "bristles" on a brush polymer and are chosen with charge properties to enhance the current blockage in the nanopore. The 4 reporter constructs each present distinct charge blocking cross-sections to the nanopores due to the length of the peptides.

It has been demonstrated that a Coulter-counter-like nanopore detector can resolve up to 5 strands of ds-DNA within its channel by monitoring current blockage (Storm, A. J. et al., "Translocation of double-strand DNA through a silicon oxide nanopore," *Physical Review. E, Statistical, Nonlinear, and Soft Matter Physics* 71(5 Pt 1): 051903, 2005). Nanopores have also resolved individual proteins of bovine serum albumin (Fologea, D. et al., "Electrical characteristics of protein molecules by a solid-state nanopore," *Applied Physics Letters* 91(5): 053901-3, 2007). At this time individual bases of native DNA have not been sequentially resolved. Polymer-based detection by nanopores is demonstrated in U.S. Pat. Nos. 6,465,193 and 7,060,507, for example, and the physical parameters of a polymer are shown to modulate electrical output from a nanopore.

In another embodiment of a nanopore-based detection apparatus (FIG. 14) the potential is applied between reservoirs A and B as described above to control S-polymer translocation; however, another circuit is added for measurement. Lateral electrodes affixed to the nanopore are used to measure impedance or conductivity across the nanopore aperture. Additional measurements such as capacitance or other electroresonant effects can be implemented in this way also. This design has an advantage of separating the translocation function from the current measurement function. As the S-polymer is conveyed through the nanopore, current modulation is again measured. (Lagerqvist, J. et al., "Influence of the environment and probes on rapid DNA sequencing via transverse electronic transport," *Biophys. J.* 106: 102269, 2007).

Microfluidic and micropipetting techniques are employed, along with drag tags, magnetic beads, electrophoretic stretching techniques, and so forth, in order to control and convey the S-polymer through the nanopore. For example, end-labeled free-solution electrophoresis, also termed ELFSE, is a method for breaking the charge to friction balance of free-draining DNA that can be used for free-solution S-polymer electrophoresis (Slater et al., "End-labeled free-solution electrophoresis of DNA", *Electrophoresis* 26: 331-350, 2005).

Methods for tethering, stretching, labeling, and measuring large DNA fragments are well established (Schwartz et al., "A single-molecule barcoding system using nanoslits for DNA analysis", *PNAS,* 104(8):2673-2678, 2007; and Blanch et al., "Electrokinetic Stretching of Tethered DNA", *Biophysical Journal* 85: 2539-2546, 2003). However, single nucleobase resolution for the purposes of whole genome sequencing of native nucleic acids is beyond the capabilities of these techniques. These techniques are applicable to S-polymer preparation for the "single-molecule" detection methods.

Figure 15:
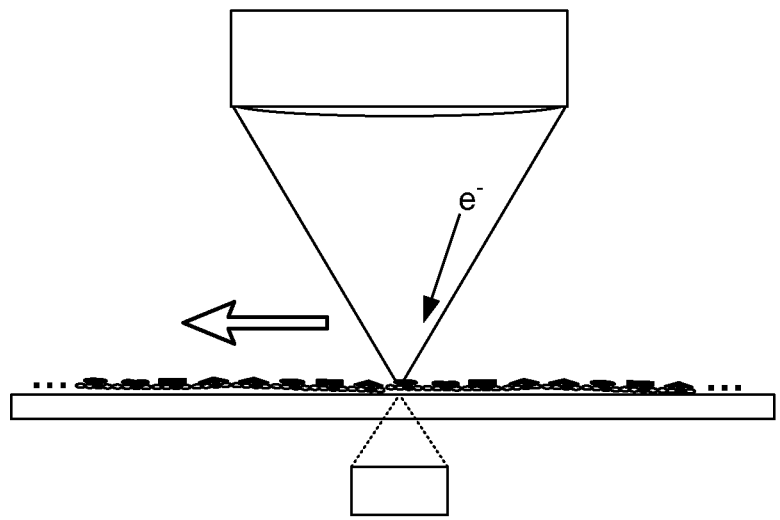
FIG. 15 illustrates detection by electron microscopy.

Detection and analysis of large DNA molecules by electron microscopy is well established (Montoliu et al., "Visualization of large DNA molecules by electron microscopy with polyamines: application to the analysis of yeast endogenous and artificial chromosomes", *J. Mol. Bio.* 246(4):486-92, 1995), however, accurate and high-throughput sequencing of polynucleotides using these methods is difficult due to high information processing requirements. In FIG. 15, transmission (TEM) is illustrated for detection of an S-polymer. Here a focused electron beam is used to scan an S-polymer, which is again generally flat on a surface. Focused electron beam reflection and scatter modes can also be adapted for S-polymer detection. Aspects of the reporter construct structures on the S-polymer serve to decode the genetic information on the backbone. Specimen fixation and sputter coating techniques, which enable imaging of individual and atom-sized features of molecules, can be used to enhance detection.

Nanoelectrode-gated electron tunneling conductance spectroscopy, in which a tunneling electron beam between two nanoelectrode tips is modulated by conveyance of the S-polymer between the tips, may also be utilized (Lee et al., "Nanoelectrode-Gated Detection of Individual Molecules with Potential for Rapid DNA Sequencing", *Solid State Phenomena* 121-123: 1379-1386, 2007). The S-polymer perturbs the tunneling current by its screening-conduction effect, which can be amplified over native DNA by use of suitable reporters. This technique has the advantage that specimen fixation and the requirement for vacuum is avoided, and in theory, massively parallel arrays of electrode gates can be employed to read many S-polymers in parallel.

Figure 16:
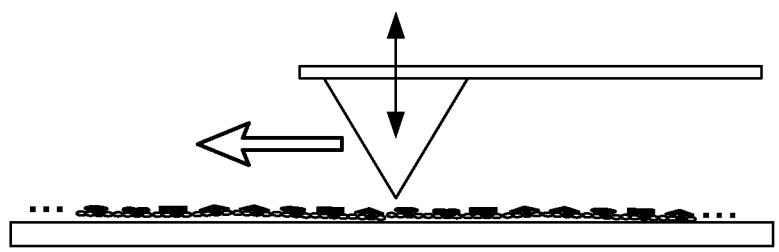
FIG. 16 illustrates detection using atomic force microscopy.

In FIG. 16, atomic force microscopy is illustrated. In a simple embodiment, a nanotube mounted on a sensitive cantilever swept across a surface and the attractive and repulsive forces between the probe and the sample surface are translated into a topological picture of the surface being scanned. This technique can achieve very high resolution but has relatively slow scan speeds (M. Miles, *Science* 277, 1845-1847 (1997)). Scanning tunneling electron microscopy (STM) is a related technology for imaging surfaces; the probe however does not touch the surface but rather a tunneling current between the surface and the probe is measured. Here the S-polymer can be laid flat on a surface and physically scanned with the probe tip.

Figure 17:
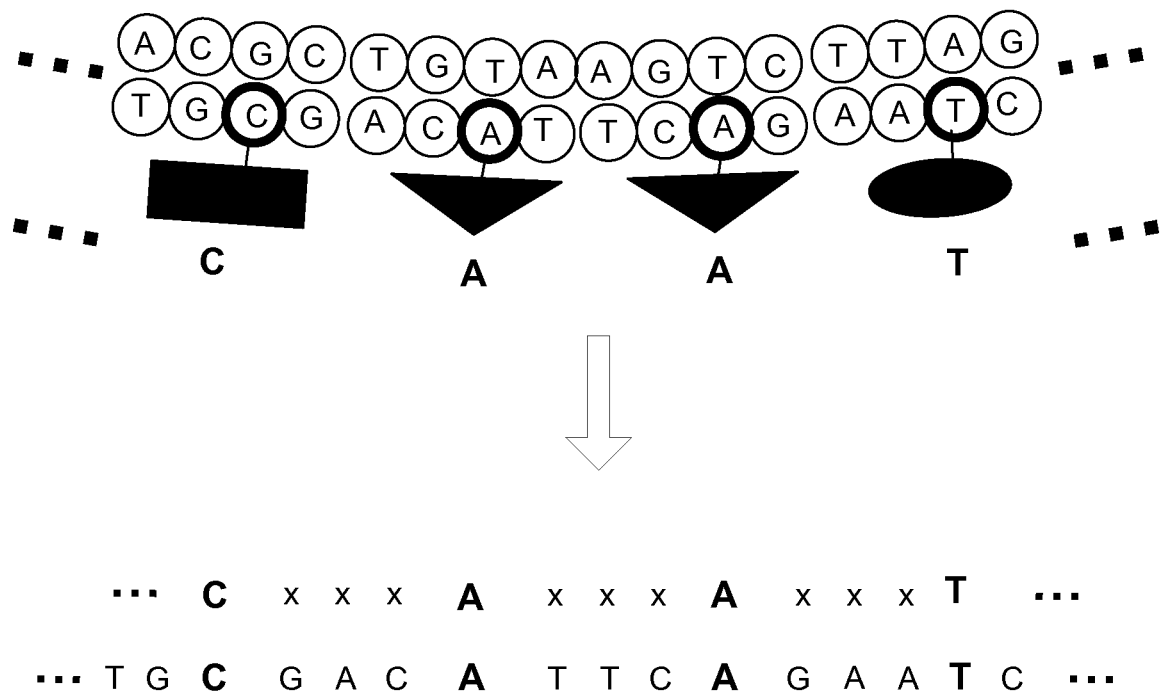
FIG. 17 illustrates a portion of an S-polymer, synthesized from tetramer S-mers that encode for single bases, duplexed to a target template.

The sequence data fragment that is produced from measuring an S-polymer is called a "read". The SSP sequence reads, adapted to include regular spaced gaps, match the sequential base information of the template (assuming no translation errors). These gaps are sized and positioned using the S-mer size and the encoded base(s) positions within the S-mer. In FIG. 17, for example, a portion of an S-polymer synthesized from tetramer S-mers that encode for single bases is shown duplexed to a target template. The read portion shown in the figure is . . . CART . . . and 3 spacers (shown as "x x x") are inserted between each base to form the spaced read . . . CxxxAxxxAxxxT . . . A "spaced read" is a read that is adjusted by adding appropriate spaces the read and accounts for the S-mer gaps of unencoded sequence. The spaced read can now be aligned with reference or other sequences (as shown at the bottom of FIG. 17). If more than 1 base is encoded in each S-mer, then spacers are added to the read sequence to reflect the S-mer probe structure and form the spaced read. It should be noted that, in this case, the reading frame of the S-mer needs to be synchronized with the read sequence, otherwise the resulting spaced read will be incorrect. Synchronization can be achieved by assigning S-mer position starting at the read ends. Alternatively, all positions could be considered and only the best fit with the rest of the data is selected. Applications for SSP sequencing include, but are not limited to, resequencing, de novo sequencing and genome fingerprinting.

Figure 18:
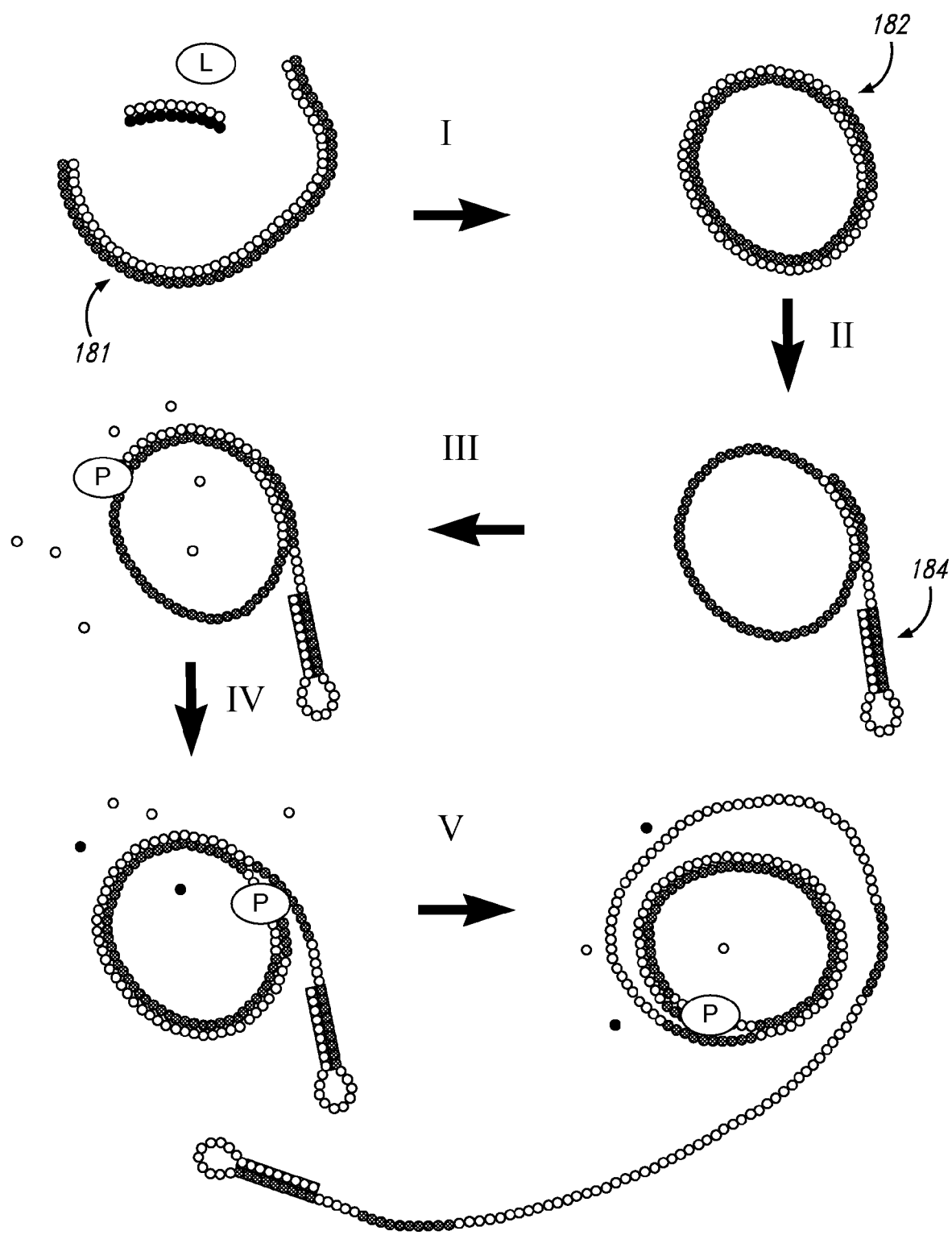
FIG. 18 illustrates S-polymer synthesis by continuous rolling circle replication of a target nucleic acid.

For resequencing applications, the published human genome reference sequence (or other reference sequence) can be used, for example, as an alignment tool to assist assembling the spaced reads. In this method, conventional matching techniques are adjusted to accommodate the gaps and the spaced reads are aligned to the reference. The fidelity of this sequence reconstruction method requires accurate sequential measurement of the S-polymer, and accurate replication of the S-polymer corresponding to the target DNA. In a similar manner to resequencing, de novo reconstruction of the target DNA can be performed by using conventional read assembly techniques that are adjusted to accommodate for the read sequence gaps. In this application, since there is no reference sequence to align to, the reads are matched against each other until clusters of consensus sequences, called contigs, are assembled. In general, this process can produce families of contigs that, when correctly interleaved, provide a portion of continuous base sequence of the target template. For some SSP products these contig families will have no sequence overlap due to their regular gap spacing. This is analogous to how odd and even numbers do not overlap and yet when correctly interleaved form the sequence of integers. To interleave and correctly position one contig to the next contig may require additional sequence data. In another application, long SSP reads can be used as a reference scaffold for assembling short sequence reads from other sequencing technologies. Another method to provide correct interleaving of the sequence reads is to prepare the primed DNA (e.g., alternative to Steps I to III in FIG. 3A) for S-polymer synthesis using rolling circle polymerization. This primed DNA strand is comprised of multiple, identical replications (referred herein as "replication units") of the parent DNA template that are connected in series. FIG. 18 depicts an example of this DNA preparation process. Double-stranded DNA is purified from a sample, fragmented (typically 1 k to 5 k base fragments), and blunt-end polished.

In FIG. 18, Step I, the target DNA fragment (181) is ligated to a double-stranded adapter oligomer to form a circularized target construct (182). In Step II, a universal hairpin primer (184) is hybridized to its complement within the adapter portion of the single-stranded, circularized target. In Step III, a strand-displacing polymerase reaction mix is added. Polymerase extension proceeds and extends from the universal primer. In Step IV, polymerase, P, has extended the nascent 3' end around the circularized template and continues for a second time around by displacing the universal primer. Step V illustrates continuous rolling circle replication. The reaction is stopped when the product is of sufficient average length. After denaturation and purification, the remaining rolling-circle product has a series of more than R replification units. A replification unit is the rolling-circle extension product portion that replicates one loop of the circularized template. The purified product is the primed DNA that is used for the S-polymer synthesis. A ligation example of S-polymer synthesis using this rolling circle product is analogous to the method shown in FIGS. 3B and S-mer incorporation proceeds from the nascent 5' end of the hairpin. An S-polymer, synthesized from S-mers which encode for single bases, will encode for the whole sequence of the circularized template provided one condition is met. For the replication unit length in bases, L, the S-mer probe length in bases, S, and the number of replication units R, the condition can be stated that: the remainders of $L/S, 2L/S, \ldots, R*L/S$ must include the numbers $0, 1, 2, \ldots, S-1$. In general when this is satisfied, the minimum R is equal to S. Each remainder is equivalent to the frame shift (in number of bases) that occurs in the S-mer position in the subsequent replication unit for the $1^{st}, 2^{nd}, \ldots$ Rth replication unit respectively. This is further equivalent to saying that a frame shift of the S-mer position occurs after each replication unit and that after R replication units, these frameshifts cause an S-mer in the S-polymer to have every position relative to a replication unit reference. As an example, consider a 5-base S-mer probe used to produce S-polymers of ~1000 base targets. Ignoring other error sources, for target lengths that have equally distributed remainders of 0, 1, 2, 3, or 4 when divided by 5 (S=5) and if R is equal to or greater than 5 then only the case with remainder zero will not generate S-polymers that encode for the entire sequence of the target DNA.

The application described above is applicable for genome fingerprinting. This application can be applied to pathogen detection, for example, where a large database of pathogen genomic sequence is used to match genomic sample sequence. If a statistically significant match of the sample sequence is found with a pathogen sequence in the database, the pathogen was found in the sample. As in the resequencing application above, the SSP spaced sequence reads can be matched against the database directly to determine if a pathogen is detected.

All of the U.S. patents, U.S. patent application publications, U.S. patent applications, foreign patents, foreign patent applications and non-patent publications (e.g., journal references) referred to in this specification and/or listed in the Application Data Sheet, are incorporated herein by reference, in their entirety. The various embodiments described above can be combined to provide further embodiments and various aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for sequencing a target nucleic acid, comprising:
a) providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a probe with X nucleobase residues, with X being a positive integer greater than one, and a reporter construct that encodes Y nucleobase residue(s) of the probe, with Y being a positive integer less than X, and;
b) detecting the reporter constructs to determine Y nucleobase(s) every X nucleobases of the daughter strand.

2. The method of claim 1, wherein X is 2 to 20.
3. The method of claim 1 wherein X is 3, 4, 5 or 6.
4. The method of claim 1, wherein X is 4.
5. The method of claim 1, wherein Y is 1 or 2.
6. The method of claim 1, wherein Y is 1.
7. The method of claim 1, wherein X is 4 and Y is 1.
8. The method of claim 1, wherein the reporter construct is joined to at least one nucleobase residue of the probe by a covalent tether.
9. The method of claim 1, wherein the reporter construct is a component of at least one nucleobase residue of the probe.
10. The method of claim 1, wherein the daughter strand is formed from a second target nucleic acid that is prepared by performing rolling circle polymerase extension of the target nucleic acid.
11. The method of claim 1, wherein the probe with X nucleobase residues comprises at least one universal base.
12. The method of claim 1, where the template-directed synthesis of the daughter strand comprises an enzymatic ligation.
13. The method of claim 1, where the template-directed synthesis of the daughter strand comprising a polymerase reaction.
14. The method of claim 1, where the template-directed synthesis of the daughter strand comprises a chemical ligation.
15. The method of claim 1, wherein the plurality of subunits in the daughter strand is greater than 30.
16. The method of claim 1, wherein the plurality of subunits in the daughter strand is greater than 1000.
17. The method of claim 1, wherein detection of the reporter constructs comprises passing the daughter strand through a nanopore.
18. The method of claim 1, wherein detection of the reporter constructs comprises interrogation with an electron beam.
19. The method of claim 1, wherein the daughter strand is duplexed with the target nucleic acid when the reporter constructs are detected.
20. The method of claim 1, wherein the daughter strand is not duplexed with the target nucleic acid when the reporter constructs are detected.
21. The method of claim 1, wherein the daughter strand is formed from a plurality of constructs having the following structure:

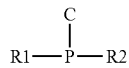

wherein
R1 and R2 represent the same or different end groups for the template synthesis of the daughter strand;
P represents the probe with X nucleobase residues; and
C represents the reporter construct that encodes Y nucleobase residue(s) of the probe.

22. The method of claim 21, wherein the R1 and R2 are individually hydroxyl, hydrogen, triphosphate, monophosphate or amine, or are an ester, an ether, a glycol, an amide, or a thioester.
23. The method of claim 21, wherein reporter C is joined to a nucleobase residue of probe P by a covalent tether.
24. The method of claim 23, wherein C comprises a polymer, dendrimer, bead, aptamer, ligand, oligomer, branched polymer, nanoparticle, and nanocrystal, or mixture thereof.
25. The method of claim 21 where reporter C is, or is a component of, a nucleobase residue of the probe.
26. The method of claim 21 wherein probe P comprises 3, 4, 5 or 6 nucleobase residues.
27. The method of claim 26, wherein reporter C encodes 1 or 2 of the P nucleobase residues.
28. The method of claim 26, wherein reporter C encodes 1 of the P nucleobase residues.
29. The method of claim 1, wherein the daughter strand has the following structure:

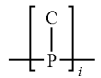

wherein
P represents the probe with X nucleobase residues;
C represents the reporter construct that encodes Y nucleobase residue(s) of the probe; and
i represents the $i^{th}$ subunit in a chain m subunits.

30. The method of claim 29, wherein m is greater than 10.
31. The method of claim 29, wherein m is greater than 100.

32. The method of claim 29, wherein m is greater than 1000.

33. The method of claim 1, wherein the daughter strand is duplexed with the target nucleic and has the following structure:

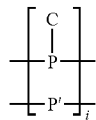

wherein

P represents the probe with X nucleobase residues;

P' represents a contiguous nucleotide sequence of X nucleotide residues of the template strand to which P is complementary;

C represents the reporter construct that encodes Y nucleobase residue(s) of the probe; and i represents the $i^{th}$ subunit in a chain m subunits.

34. A kit comprising a plurality of unique constructs for forming a daughter strand by a template-directed synthesis and optional instructions for use of the same, wherein the daughter strand to be formed by the template-directed synthesis comprises a plurality of subunits coupled in a sequence corresponding to a contiguous nucleotide sequence of all or a portion of a target nucleic acid, wherein the individual subunits comprise a probe with X nucleobase residues and a reporter construct the encodes Y nucleobase residue(s) of the probe, and wherein each of the plurality of constructs are the same or different and individually have the following structure:

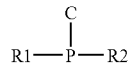

wherein

R1 and R2 represent the same or different end groups for the template synthesis of the daughter strand;

P represents the probe with X nucleobase residues, with X being a positive integer greater than one; and C represents the reporter construct that encodes Y nucleobase residue(s) of the probe, with Y being a positive integer less than X.

35. The kit of claim 34, wherein the R1 and R2 are individually hydroxyl, hydrogen, triphosphate, monophosphate or amine, or are an ester, an ether, a glycol, an amide, or a thioester.

36. The kit of claim 34, wherein reporter C is joined to a nucleobase residue of probe P by a covalent tether.

37. The kit of claim 34, wherein C comprises a polymer, dendrimer, bead, aptamer, ligand, oligomer, branched polymer, nanoparticle, and nanocrystal, or mixture thereof.

38. The kit of claim 34, where reporter C is, or is a component of, a nucleobase residue of the probe.

39. The kit of claim 34, wherein probe P comprises 3, 4, 5 or 6 nucleobase residues.

40. The kit of claim 34, wherein reporter C encodes 1 or 2 of the P nucleobase residues.

41. The kit of claim 34, wherein reporter C encodes 1 of the P nucleobase residues.

42. The kit of claim 34, wherein the plurality of unique constructs range in number from 10 to 65000.

43. The kit of claim 34, wherein the plurality of unique constructs range in number from 50 to 5000.

44. The kit of claim 34, wherein the plurality of unique constructs range in number from 200 to 1200.

* * * * *